United States Patent [19]
Hobbs et al.

[11] Patent Number: 5,896,855
[45] Date of Patent: Apr. 27, 1999

[54] MULTI DOSE INHALER APPARATUS

[75] Inventors: Michael A. Hobbs; John R. Calvert; Robert S. Cook; Roy Trunley; Gordon T. Simpkin, all of Dagenham, United Kingdom

[73] Assignee: Rhone-Poulenc Rorer Limited, West Malling, United Kingdom

[21] Appl. No.: 08/481,026

[22] Filed: Jun. 7, 1995

Related U.S. Application Data

[63] Continuation-in-part of application No. PCT/GB93/02642, Dec. 23, 1993.

[30] Foreign Application Priority Data

Dec. 24, 1992 [GB] United Kingdom ............ 9226901
Dec. 24, 1992 [GB] United Kingdom ............ 9226918
Dec. 24, 1992 [GB] United Kingdom ............ 9226951
Dec. 24, 1992 [GB] United Kingdom ............ 9226969

[51] Int. Cl.$^6$ ............................................. A61M 15/00
[52] U.S. Cl. ........................... 128/203.15; 128/203.21; 128/203.12
[58] Field of Search ............... 128/200.24, 203.15, 128/203.21, 203.12, 203.23

[56] References Cited

U.S. PATENT DOCUMENTS

| | | | |
|---|---|---|---|
| 4,674,651 | 6/1987 | Scidmore | 221/3 |
| 4,809,877 | 3/1989 | Albright | 227/15 |
| 4,838,453 | 6/1989 | Luckstead | 221/2 |
| 5,048,514 | 9/1991 | Ramella | 128/203.21 |
| 5,152,284 | 10/1992 | Valentini et al. | 128/203.21 |

FOREIGN PATENT DOCUMENTS

| | | |
|---|---|---|
| 0 406 893 | 1/1991 | European Pat. Off. . |
| 0 424 790 | 5/1991 | European Pat. Off. . |
| 0 506 293 | 9/1992 | European Pat. Off. . |
| 1387954 | 3/1975 | United Kingdom . |
| 1472650 | 5/1977 | United Kingdom . |
| 1562732 | 3/1980 | United Kingdom . |
| 2061735 | 5/1981 | United Kingdom . |
| 2151491 | 7/1985 | United Kingdom . |
| 2189914 | 11/1987 | United Kingdom . |
| 2242134 | 9/1991 | United Kingdom . |
| 2255918 | 11/1992 | United Kingdom . |
| 82/01470 | 5/1982 | WIPO . |
| 92/03175 | 3/1992 | WIPO . |

*Primary Examiner*—V. Milliai
*Assistant Examiner*—Kelly O'Hara
*Attorney, Agent, or Firm*—Ross J. Oehler, Esq.

[57] ABSTRACT

An inhaler for inhalation of a medicament from a pierced capsule has a swirling or emptying chamber where the capsule is emptied by inhalation action of an operator. A rotary magazine for a multi-unit does inhaler which holds a number of capsules containing a medicament in a number of recesses arranged around the periphery of the magazine. The capsules are held in place by pins or plugs at both ends. Either the capsules are pierced before being loaded into the magazine or they are pierced by the pins when they are loaded into the magazine. In either case a seal may be provided around the ends of the capsules near the holes which are plugged to keep them fresh. When a recess is rotated to a particular position within the magazine then it releases its capsule. Contents of a capsule are drawn out during inhalation when the capsule is in the swirling chamber. A motor can be used to operate the magazine.

40 Claims, 20 Drawing Sheets

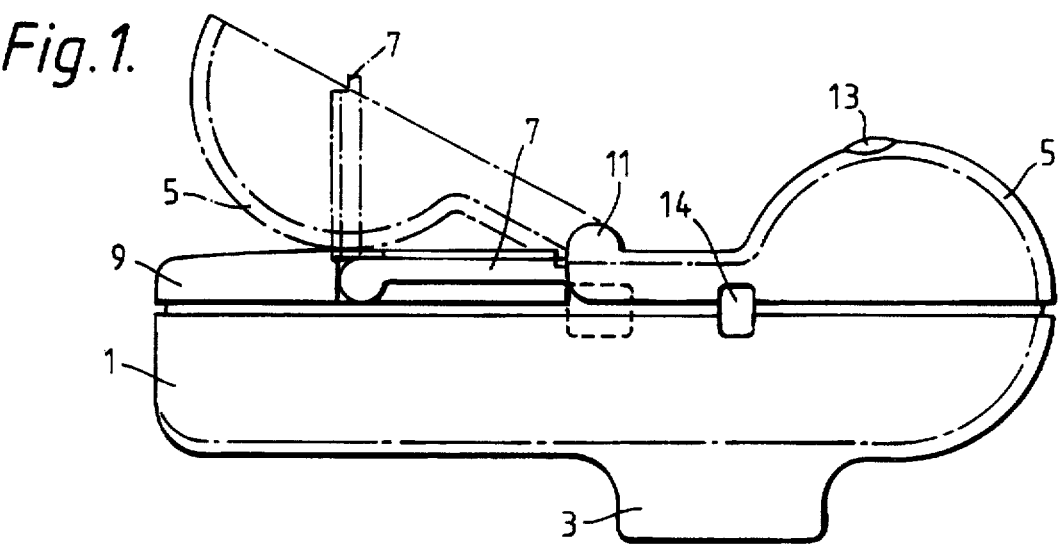
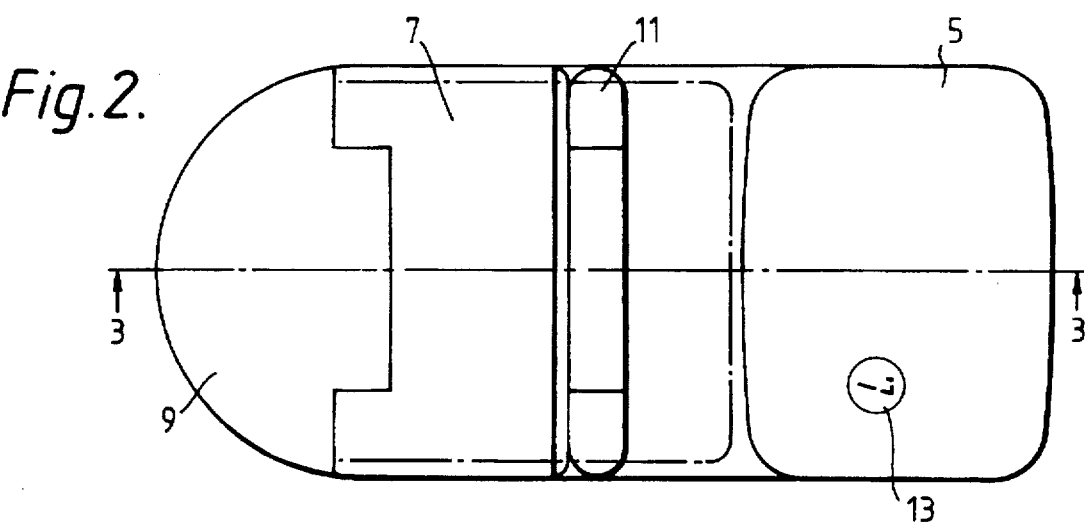
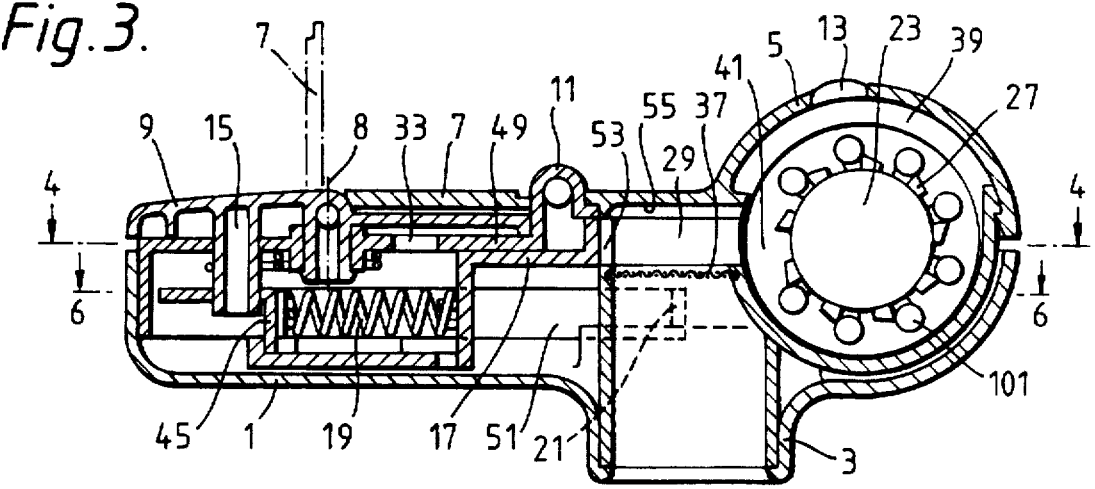

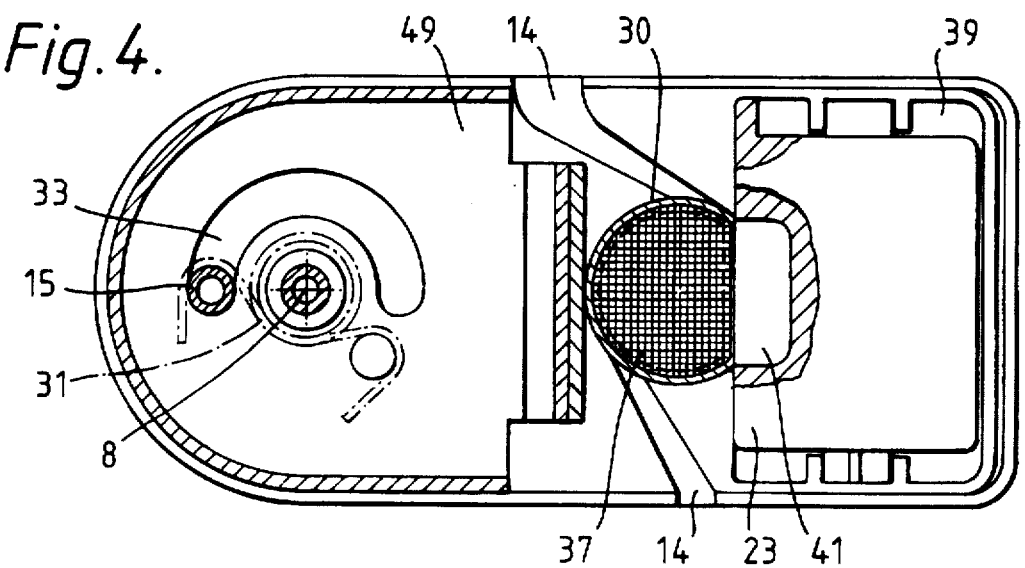
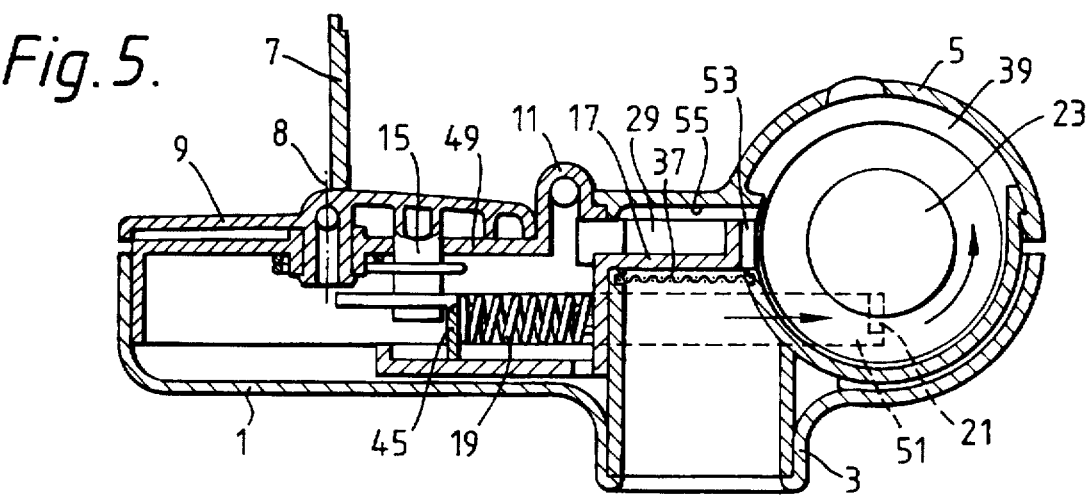
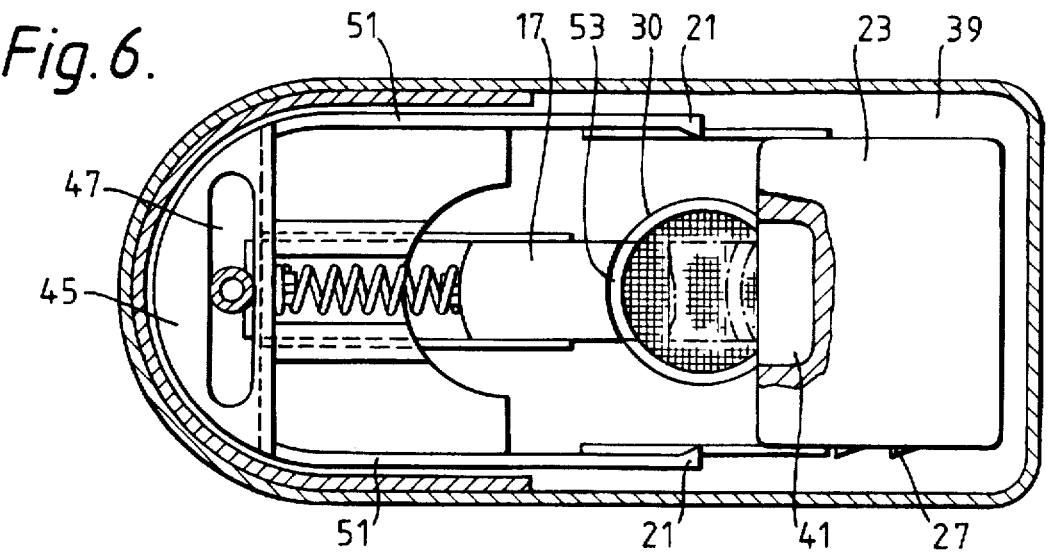

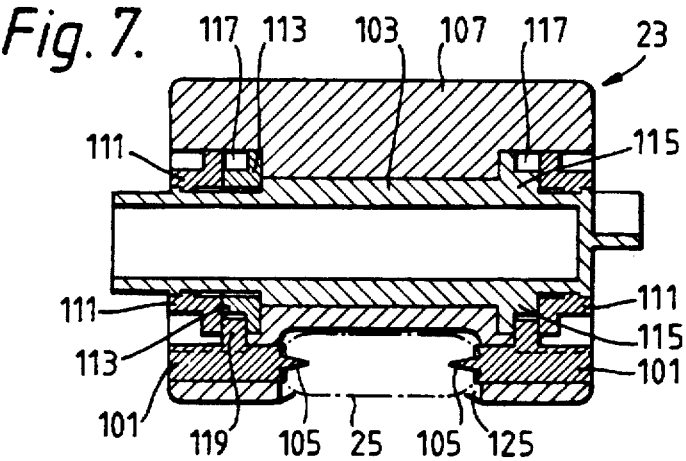
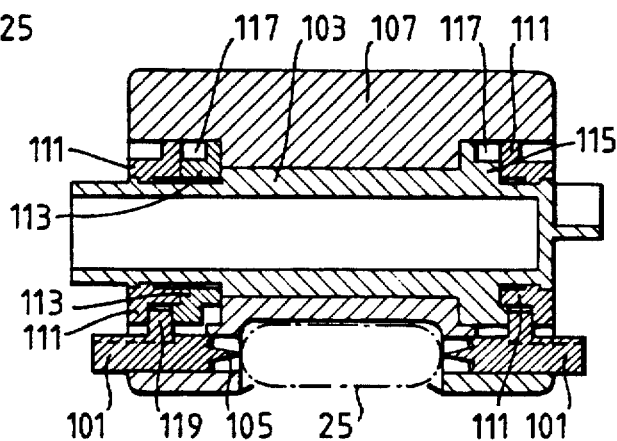
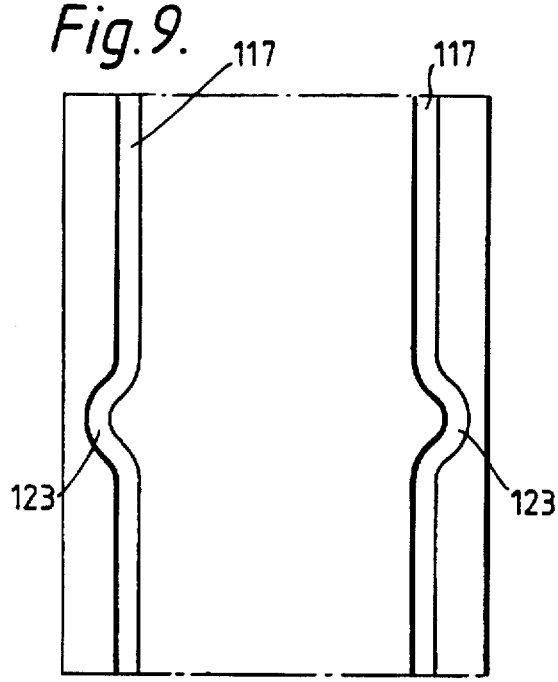
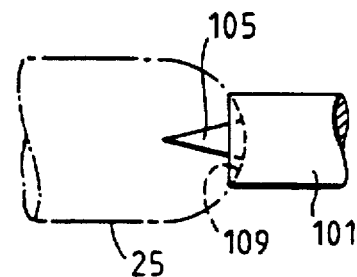
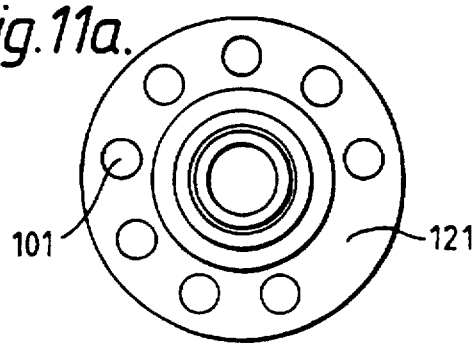
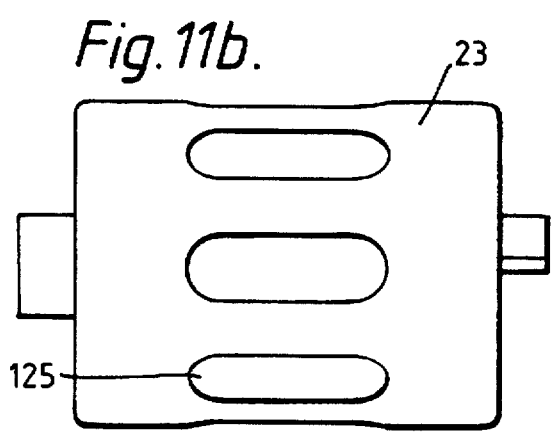

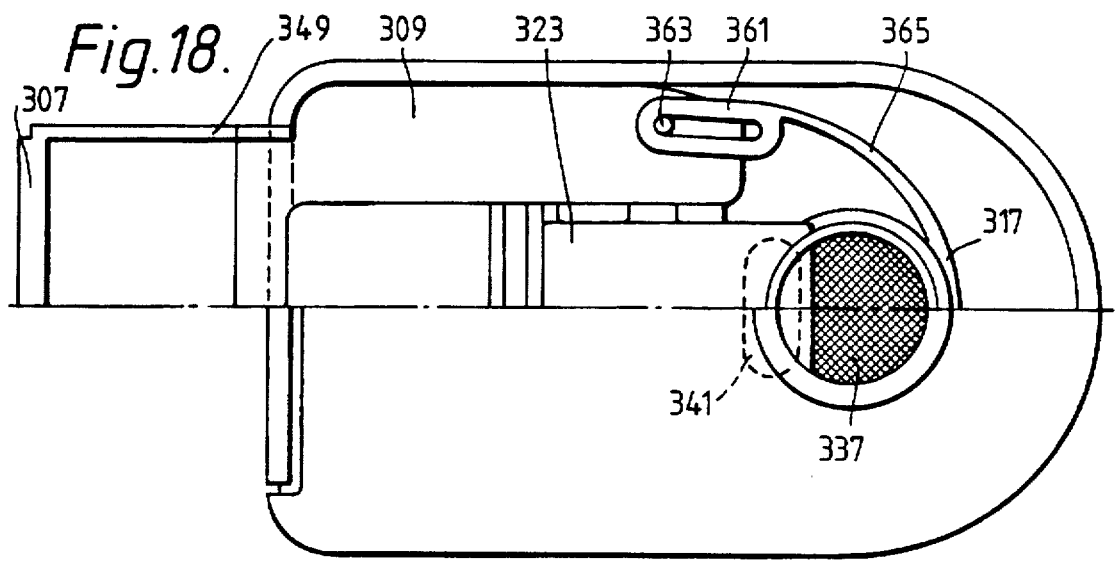
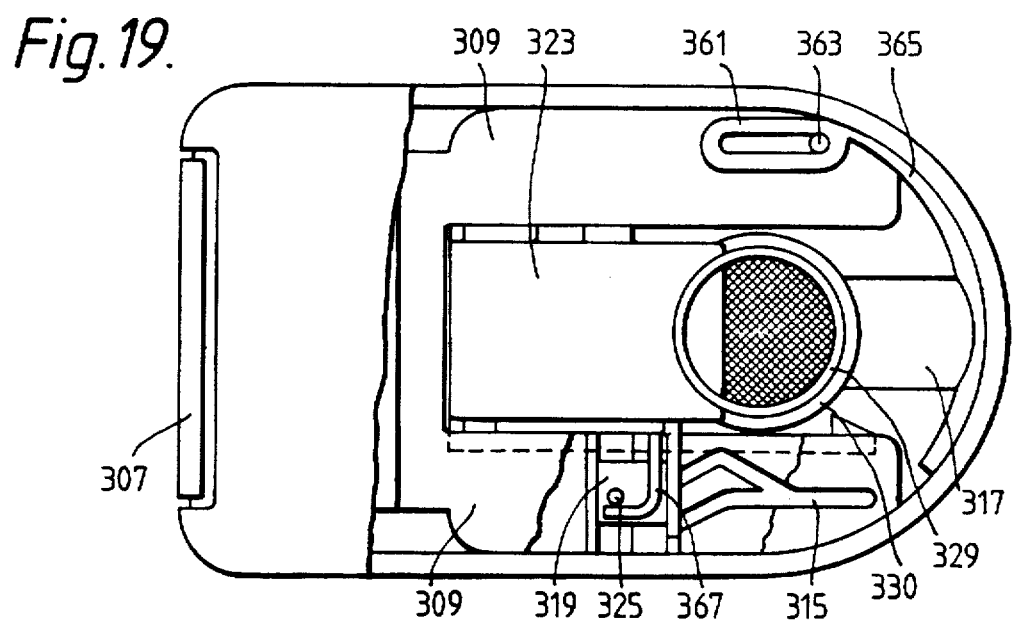
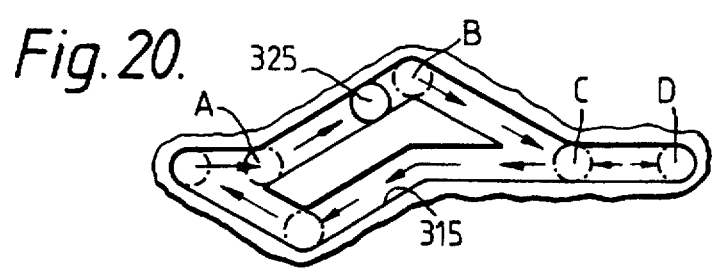

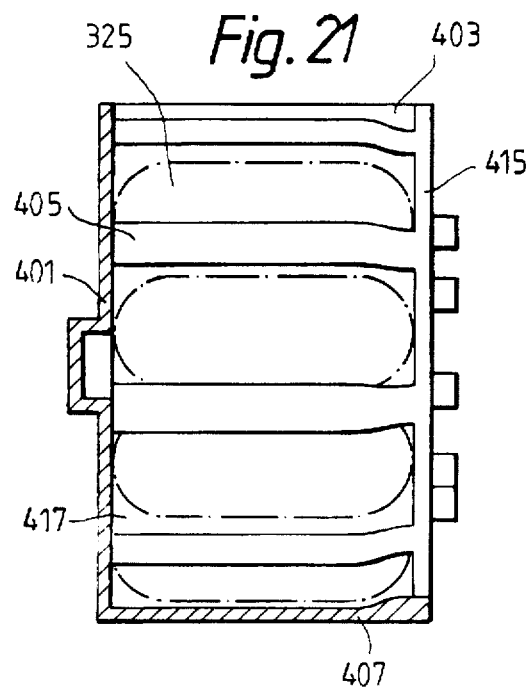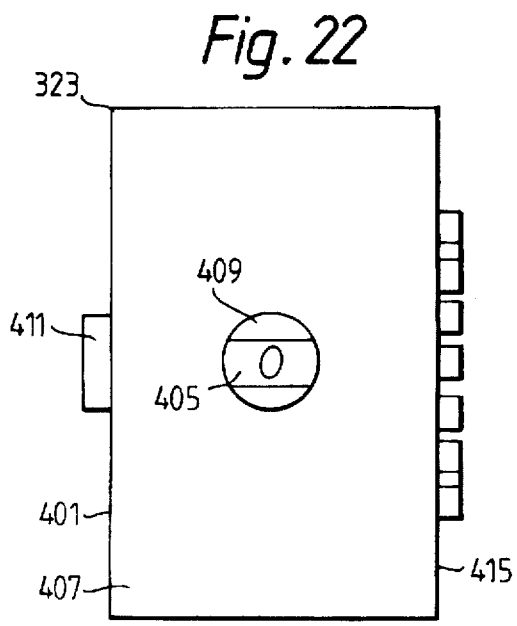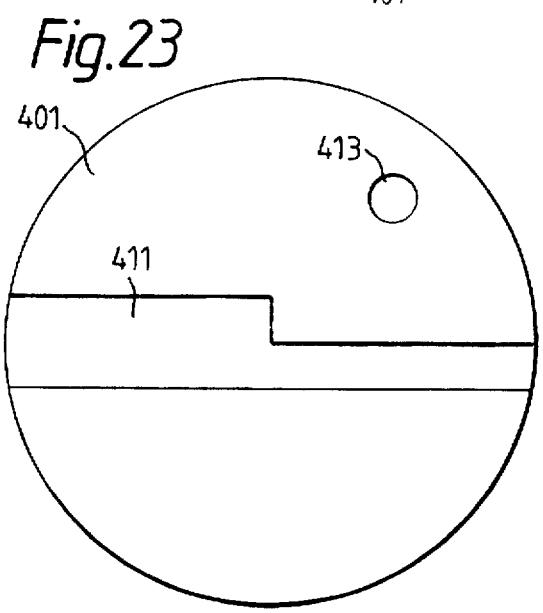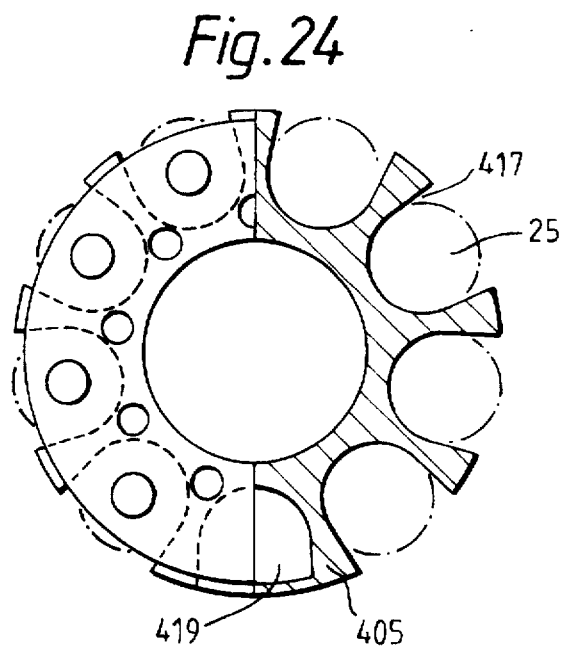

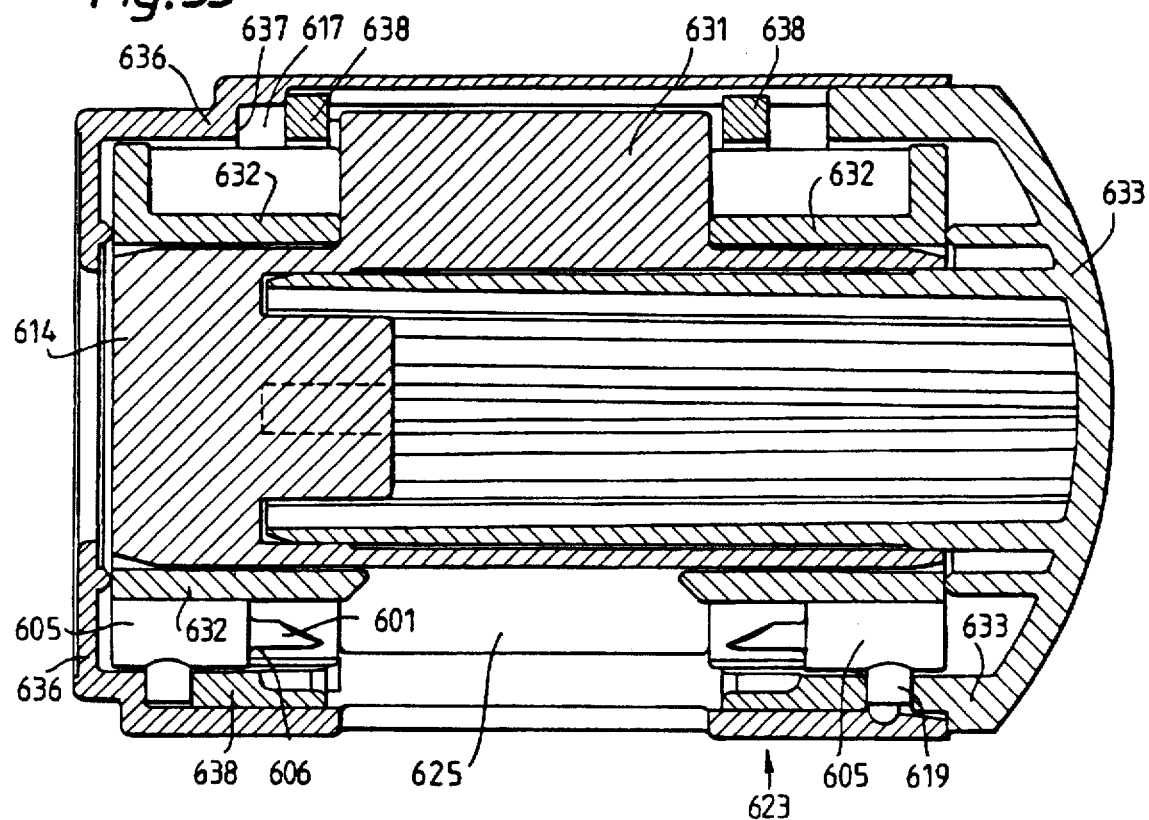
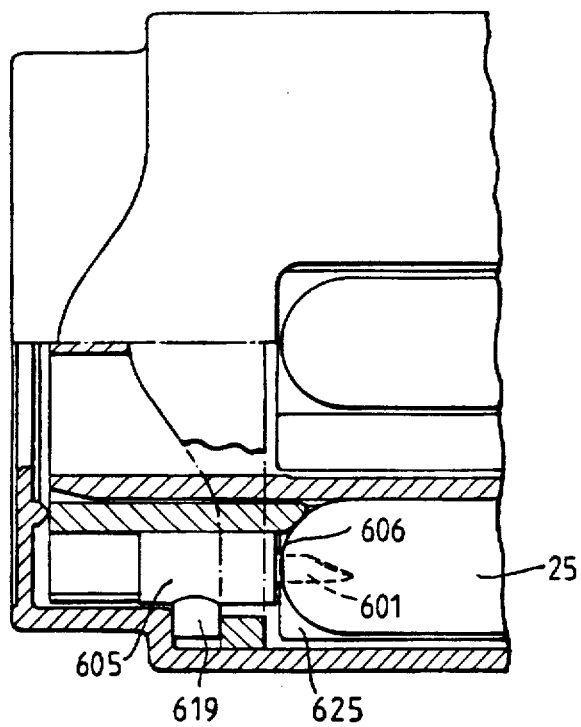

MULTI DOSE INHALER APPARATUS

This application is a continuation-in-part of PCT/GB93/02642 filed Dec. 23, 1993.

FIELD OF THE INVENTION

The present invention relates to inhalers for the inhalation of a medicament, usually pulverulent, from a container, for example a hard gelatin capsule, and more specifically to inhalers with magazines containing several capsules to be used one at a time.

BACKGROUND OF THE INVENTION

Various forms of multi-unit does inhalers are known and among these are ones in which a main housing contains a blister pack. The blister pack has a plurality of blisters each defining a container having a dosage of medicament and which are burst individually in order for a user to inhale the medicament. The blisters remain joined to a carrier during extraction of the medicament.

Further multi-unit does inhalers include those using capsules which are held in a rotating magazine. One end of a capsule is pulled away from the other to allow access of air to the contents, whereby they can be inhaled. Alternatively the capsules may be pierced to gain access to their contents after which the user may inhale the medicament.

In such an arrangement the extraction of medicament usually occurs as a result of an inhaled airstream passing over a capsule or other container.

It is necessary to provide access to the contents of a capsule or blister pack. This can be done by piercing the container, which may lead to the drawback of needing to provide piercing pins in the inhaler and which, if an inhaler is handled carelessly, could cause discomfort. Also, if a container is pierced in situ it can lead to fragments of the container being inhaled with the contents.

It is a disadvantage of most known inhalers that not all of the medicament, or even a large proportion of it, is drawn from the capsule, or the separated capsule cap and body portions, or the blister pack.

It is known that a swirling chamber using a combination of pneumatic action, centrifugal action, and impact to extract medicament from a capsule is very effective and it is preferred that the inhaler should be capable of using such actions in such a swirling chamber without over-complicating the device.

Preferably a capsule should be automatically loaded and pierced without loss of contents prior to entry into the medicament chamber.

However, the spent capsules must then be removed in order to allow access for the next unused capsule.

It is a disadvantage of known inhalers that it is often necessary to carry out many manipulative movements and capsule transfers before the medicament can be inhaled. In the case of someone who is unable, especially at the time the medicament is most needed, to perform all these functions these known inhalers can be inconvenient.

Further, it is not often, if ever, clear how many capsules a magazine has still left. Even if it can be seen how many are left, if all the capsules have been used it will still be possible for the user to attempt to inhale (on a used capsule).

BRIEF SUMMARY OF THE INVENTION

It is an object of the present invention to provide an efficient multi-unit does inhaler in which at least some of the above mentioned disadvantages are eliminated.

According to a first aspect of the present invention this object is met by a rotary magazine for use in an inhaler, comprising a plurality of recesses for holding pierced capsules, means for holding the capsules, means for plugging pierced holes in the capsules, and means to release said capsules one at a time from said magazine, wherein said holding means and plugging means are provided in a plurality of individual recesses.

Preferably a capsule should be automatically loaded into the magazine and plugged, without loss of contents prior to entry into the medicament chamber.

According to a second aspect of the present invention there is provided an inhaler comprising a capsule-emptying chamber, a nozzle through which air can be exhausted from said capsule-emptying chamber by inhalation, and ejecting means for removing a capsule from the capsule-emptying chamber into storage means within the inhaler.

According to a third aspect of the present invention there is provided an inhaler comprising a swirling chamber having first and second generally parallel opposed walls and a peripheral wall with a chordal chamber recess therein, a nozzle through which air flow through said chamber can be induced by inhalation, and a magazine having recesses for capsules to be presented to said chamber by movement transversely of their lengths; wherein said first and second walls are spaced apart by less than the length of the magazine recesses, the width of the swirling chamber is greater than the length of the magazine recesses, and said magazine recesses are sequentially presented to said chamber to form the chordal chamber recess.

According to a fourth aspect of the present invention there is provided an inhaler comprising a capsule-emptying chamber, a nozzle through which air can be exhausted from said capsule-emptying chamber by inhalation, a magazine for providing one capsule at a time from a plurality of capsules to the capsule-emptying chamber through a use position in said magazine, and a motor for controlling operation of the magazine and provision of capsules to the capsule-emptying chamber.

It is a further intention that inhalers according to the present invention should need as little cleaning as possible and should be made of suitable materials.

It is very useful to know how many capsules or doses are left in an inhaler before it needs to be recharged and therefore an indicator, either electrical or mechanical, may be provided on the magazine or the inhaler.

The inhalers of the present invention are intended to be carried in a pocket and therefore are preferably reasonably compact and portable. Moreover, they should be convenient to use.

The inhaler can be used with capsules which are pierced before they are loaded into the magazine, or pierced in the magazine, or pierced just before use. In any such case it is intended that no fragments of capsule shell should be inhalable.

It is envisaged that the inhaler should be reusable and take clips or magazines loaded with capsules. Each of the magazines should hold a plurality and preferably at least eight such capsules.

With the third and fourth aspects, after it has been used, a spent capsule can be transferred to an integral storage/disposal container, and preferably this should be by transfer back into the magazine.

BRIEF DESCRIPTION OF THE DRAWINGS

In order that the present invention may be more readily understood the following description is given, merely by way of example, with reference to the accompanying drawings, in which:

FIG. 1 is a side elevational view of a first inhaler embodiment for use with a magazine in accordance with the present invention;

FIG. 2 is a top plan view of the inhaler of FIG. 1;

FIG. 3 is a side sectional view taken along the line 3—3 of FIG. 2;

FIG. 3a is a side sectional view taken along the line 3a—3a of FIG. 2a;

FIG. 4 is a sectional view taken along the line 4—4 of FIG. 3;

FIG. 4a is a sectional view taken along the line 4a—4a of FIG. 3a;

FIG. 5 is a view similar to FIG. 3 but showing the inhaler, partway through the operating cycle when the capsule magazine has just been rotated;

FIG. 6 is a bottom sectional view taken along the line 6—6 of FIG. 3;

FIG. 7 is a side sectional view of a first rotary magazine embodiment in accordance with the present invention for use in the inhaler of FIG. 1;

FIG. 8 is a view of the same section as FIG. 7 when the magazine has been rotated to a position where a capsule is ready for use;

FIG. 9 is a development view of the capsule release cam tracks of the magazine of FIGS. 7 and 8;

FIG. 10 is an enlarged view of part of FIG. 7;

FIG. 11a is an end elevational view of the magazine of FIG. 7;

FIG. 11b is a side elevational view of the magazine of FIG. 7;

FIG. 18 is a split view showing in one half a top plan view of FIG. 15 and in the other a top plan view of the inhaler of FIG. 15 part way through the 'use cycle' with the top cover removed;

FIG. 19 is a top view of the inhaler of FIG. 15 looking at various sections through the depth of the inhaler;

FIG. 20 is an enlarged view of a cam track shown in FIG. 19;

FIG. 21 is a side sectional view of a third rotary magazine embodiment for use in the inhaler of FIG. 15;

FIG. 22 is a side elevational view of the magazine of FIG. 21;

FIG. 23 is an end elevational view of the magazine of FIG. 22;

FIG. 24 is a split view showing on one side an end elevational view of the magazine of FIG. 22 and on the other side an end sectional view of the magazine of FIG. 22;

FIG. 33 is a longitudinal transverse section of a fourth embodiment of the capsule magazine in accordance with the present invention;

FIG. 34 is a partly sectioned elevational detail of the left hand end of the magazine of FIG. 33;

DETAILED DESCRIPTION OF PREFERRED EMBODIMENTS

Figure 2A:
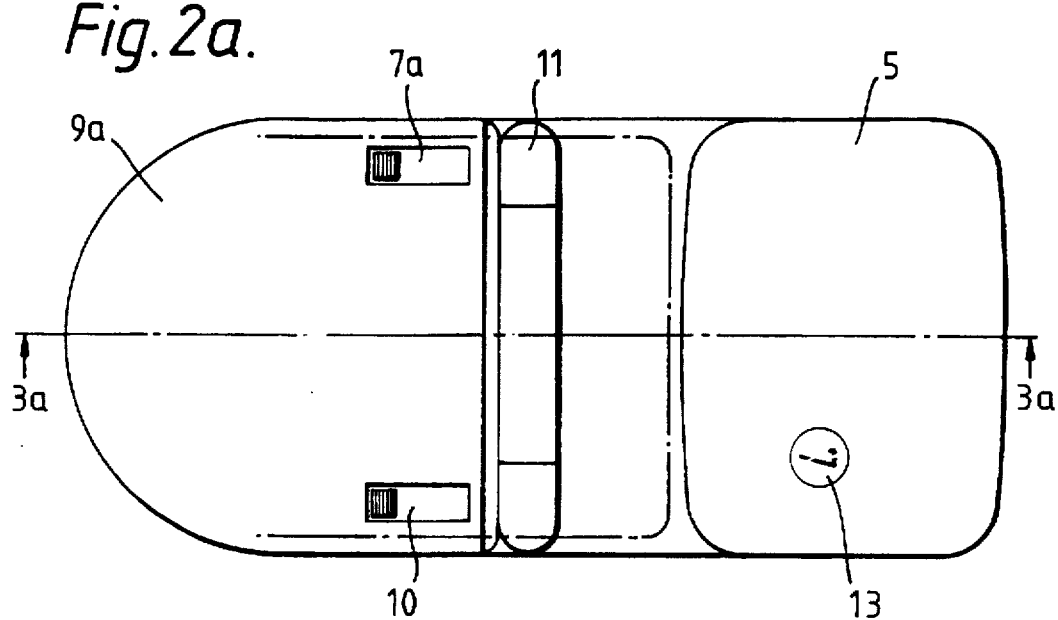
FIG. 2a is a top plan view of a motorized variant of the inhaler of FIG. 1.

Referring now to the drawings, wherein the numerals indicate like elements throughout, a first embodiment of the present invention will be described with reference to FIGS. 1, 2, 3, 4, 5 and 6.

A motorized variant will also be described with reference to FIGS. 2a, 3a, 4a and 5a which are views corresponding to FIGS. 2 to 5 but showing different drive mechanisms.

Referring now to the drawings, a first embodiment of an inhaler according to the present invention will be described with reference to FIGS. 1 to 6. The inhalers of the first embodiment are for using magazines with capsules which do not need to be pierced by pins provided in the inhaler at the moment of preparation but are already pierced in the magazines.

FIG. 1 shows a side view of an inhaler according to a first embodiment of the present invention. From FIGS. 1 to 3 it can be seen that there is a main body (1) from one face of which protrudes a mouthpiece nozzle (3) through which medicament held in capsules is drawn out and delivered to a user in a capsule-emptying phase, taking place in a swirling chamber (29) in the main body. On the other face of the main body from the mouthpiece nozzle (3) is situated the magazine chamber cover (5) rotatable about a pivot (11). When the magazine chamber cover (5) is opened, a used rotary magazine (23) of spent medicament capsules can be removed from the magazine chamber (39) and/or a new one inserted. Also accessible from the outside there is provided a key (7) which is pivoted at one end about a first axis and may be lifted up to the position shown by the dotted lines in FIG. 1. The key (7) is further pivoted to rotate about a vertical second axis (8). Turning this key (7) about the vertical axis (8) operates the mechanism of the inhaler to eject a used capsule from the swirling chamber (29) shown in FIG. 6, and to replace it with an unused capsule from the magazine for the operator to use.

There are two air inlets (14) (FIG. 1) on the sides of the main body (1). When the user inhales through the mouthpiece nozzle (3) air is drawn in through these inlets (14) into the swirling chamber (29) where it picks up the contents of a capsule and exhausts them through a mesh (37) and the nozzle (3).

An alternative embodiment of the present invention, where it is desired to use a motorized inhaler, is shown in FIG. 2a which is a top view of this embodiment of inhaler. The cover plate (9a) has on it the controls for the inhaler. Two switches are shown; the first (7a) is for operating the motor to work the mechanism of the inhaler to eject a used capsule from the capsule-emptying or swirling chamber (29), shown in FIG. 3a, and to replace it with an unused capsule from the magazine for the operator to use; the second switch (10) is for opening the chamber cover (5).

Figure 4A:
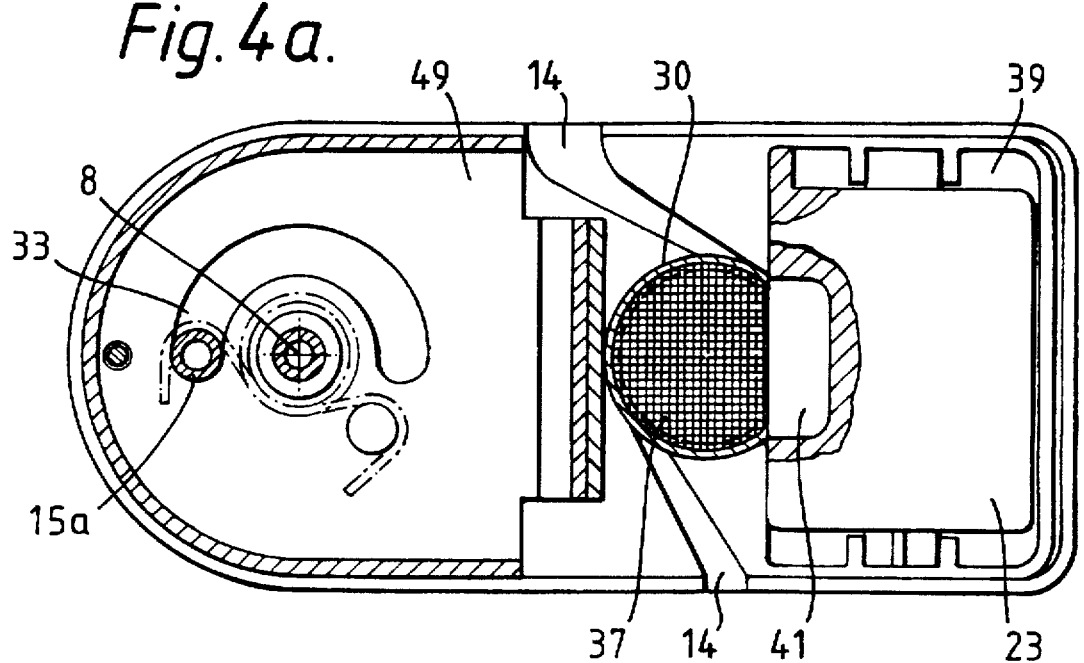
Figure 5A:
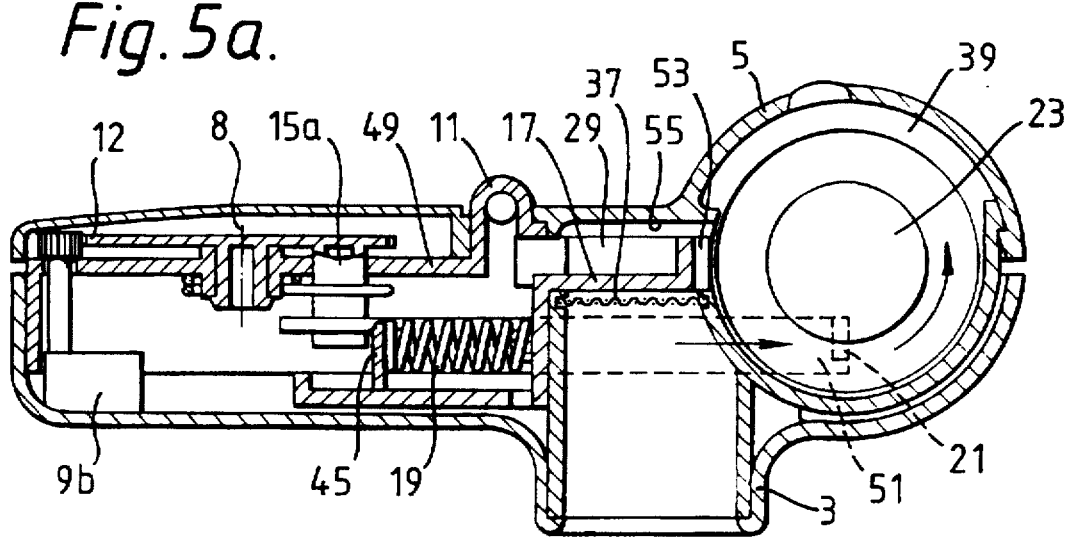
FIG. 5a is a view similar to FIG. 3a but showing the motorized inhaler, partway through the operating cycle when the capsule is returned and held in the magazine.

The operation of the non-motorized embodiment, whereby a capsule which has been used and is left in the swirling chamber (29) is removed and replaced by an unused capsule from the rotary magazine (23), will be described with reference to FIGS. 3, 4, 5 and 6, and to FIGS. 3a, 4a and 5a.

When the operator wishes to use the manual type of inhaler he lifts the key (7) to its vertical position and rotates it about the vertical axis (8) in a clockwise direction.

Alternatively, in the motorized embodiment, the operator operates the first switch (7a) to operate the motor (9b) which, through gears or other means, rotates horizontal plate (12) about the vertical axis (8) in a clockwise direction.

In the non-motorized version, there is also provided a cover plate (9) on the outside of the inhaler, which is flush with the key (7) in its horizontal position. In rotating the key (7) the cover plate (9), pivotally attached to the key (7), is also caused to rotate. Formed as part of, or attached to, the cover plate (9) is a peg (15) which protrudes into the inhaler.

Figure 3A:
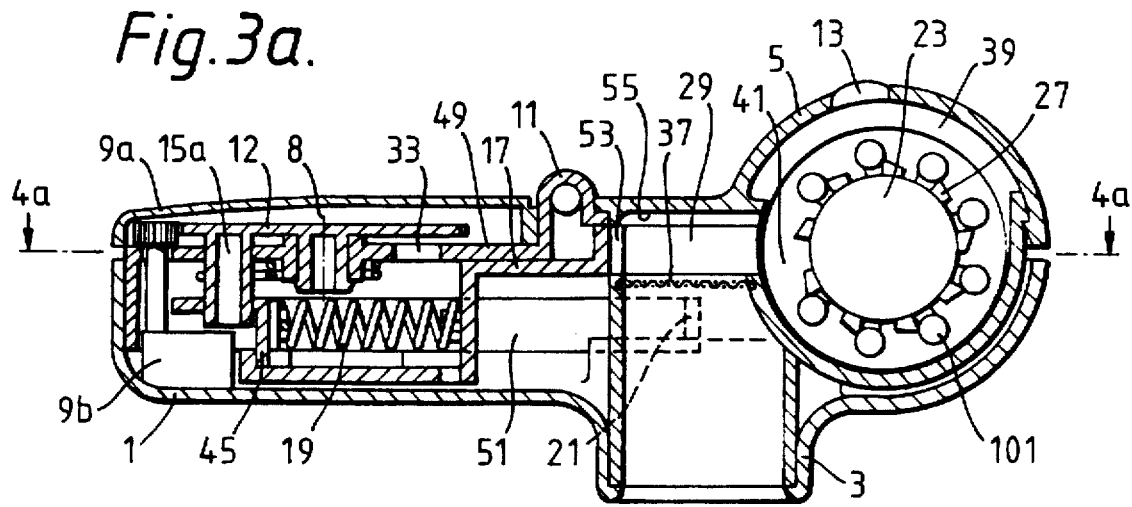

In the motorized embodiment, pet (15a) is formed with the horizontal plate (12), protruding into the inhaler (FIG. 3a).

The peg 15 or 15a is slotted through an arcuate track (33) formed in an inner frame (49) situated within the main body (1) at an end remote from the magazine chamber (39), and is caused to travel along the arcuate track (33) against the resistance of a spring (31), as the key (7) is turned. The peg (15) also passes through a rectilinear track (47) as can be seen from FIG. 6. The rectilinear track (47) is formed in the flat rear part of a movable slide plate (45) situated within the main body. As the peg (15) is rotated around the arcuate track (33) it passes back and forth along the rectilinear track (47) and moves the slide plate (45) forwards, that is to the right in FIGS. 3 to 6.

As part of, or attached to, the slide plate (45) are driven arms (51) for rotating the rotary magazine (23). Also attached to the slide plate (45), through an optional compression spring (19), is a movable capsule ejector plate (17). The ejector plate (17) is movable across the width of the swirling chamber (29). If desired in a motorized embodiment, the motor (9b) may instead drive the ejector plate (17) in both directions, and the spring (19) can be omitted.

As can be seen from FIG. 5, when the key (7) and peg (15) are rotated about the vertical axis (8) the slide plate (45), the driven arms (51) (shown in dotted lines in FIG. 5) and the ejector plate (17) are advanced. Before the slide plate (45) reaches the position shown in FIG. 5 the ejector plate (17) reaches the limit of its possible movement and is prevented from travelling any further. From this point the peg (15) may only travel further along the arcuate track (33) against the resistance of the compression spring (19) as it is compressed. By this further movement the driven arms (51) advance further whilst the ejector plate (17) is stationary.

The forward motion of the driven arms (51) causes the rotary magazine (23) to index by rotating in an anti-clockwise direction, as seen in the orientation of FIG. 5, as ratchet pieces (27), formed on both sides of the rotary magazine (23), are caught by protrusions (21) on the driven arms. Once the peg (15) has reached the limit of its movement along the arcuate track and is released, the two springs (19) and (31) rotate it back to the other end of the arcuate track. At the same time the slide plate (45), with the arms (51), and the ejector plate (17) return to their original positions. On the retraction of the driven arms (51) the rotary magazine (23) does not rotate back in a clockwise direction but stays where it has been advanced to by the protrusions (21). Either the magazine itself or the magazine in combination with the magazine chamber (39) is provided with means (not shown) by which this is achieved. Further, means could be used to ensure that a magazine is rotated neither more nor less than the amount necessary for the magazine to feed a new capsule to the emptying or swirling chamber.

During its movement the ejector plate (17) is advanced into the swirling chamber (29) by the rotation of the key (7) (or motor (9b) and rotating plate (12)) about the vertical axis (8). The ejector plate (17) has an end tab (53) seen in FIGS. 3, 5 and 6. When the ejector plate (17) is in its rest position the end tab (53) forms part of the chamber wall (30) of the swirling chamber (29). Whilst the end tab (53) may be flush with the wall when at rest, it may instead protrude from, or form a recess in, the wall in order to provide irregular surfaces on which, during the inhalation of a medicament from a capsule as described later, a capsule may sustain further impacts. It is preferred that no gaps should be found around the edges of the end tab (53) as it sits in its rest position, so that during inhalation no air may leak past it into the swirling chamber (29) and thereby reduce the swirling effect of the air entering through inlets (14). Also no powder from capsules may work its way into the mechanism and thereby cause a need for more regular cleaning. Preferably a seal is formed between the chamber wall (30) and the edges of the end tab (53). A capsule is trapped in the swirling chamber by a mesh (37) below it, a top wall (55) above it and the peripheral side wall (30).

As the ejector plate (17) with the end tab (53) is advanced by the turning of the key (7) it crosses the diameter of the swirling chamber (29) and pushes any capsule in the swirling chamber (29) towards a chordal recess (41) formed opposite to the end tab (53) and which is part of the rotary magazine (23) and from which, in most cases, the capsule entered the swirling chamber (29). The end tab (53) is arcuate in shape whereby no capsule should be longitudinally trapped between the end tab (53) and the back wall of the recess (41), but instead an end of the capsule slides along the tab (53) and enters the recess (41) along its length. In this fashion, used capsules are removed from the swirling chamber (29) with no need for them to be removed by hand and no ejection of them into the environment. This could otherwise both pollute the environment and present a hazard.

The end tab (53) advances until it has reached its movement limit position, which is defined to be just before it reaches the rotary magazine (23), so that it does not inhibit rotation of that magazine. Any capsule in the swirling chamber (29) would, by the time the end tab has reached its limit position, have been forced into the chordal recess (41) provided at the side of the swirling chamber by the rotary magazine. Further, because the end tab (53) is maintained at its limit position as the magazine (23) is rotated, the capsule is kept by the end tab (53) in its recess (41) as long as is necessary to prevent its escape, that is until after indexing rotation. Apart from at the use position, when a recess (41) in the rotary magazine (23) forms a recess in the swirling chamber (29), the capsules should not be released from the magazine. Once a rotary magazine (23) has been rotated, and the key (7) is released or turned back to its original position, the slide plate (45) also returns towards its original position causing the arms (51) and ejector plate (17) to do so too.

Where a motorized embodiment is used, once the magazine has been rotated through one recess interval, circuitry with the motor (9b) detects this and reverses the direction of rotation of the rotating plate (12) to similarly return slide plate (45) to its original position. This allows a capsule newly rotated to the use position, to be used.

While, in the drawings, the key (7) is to be rotated about its vertical axis (8) in a clockwise direction there is no reason why the inhaler (or motor therefor) could not be manufactured for the key (or rotating plate) to be rotated in an anti-clockwise direction for use by left-handed people, or for use even in either direction. Further, although the peg (15) is shown to travel back and forth around a semi-circular arcuate track (33), it could travel 360° around a circular, or possibly elliptical track in the course of a single cycle. This may be preferable for a motorized embodiment for cutting down on extra circuitry. Alternatively, the motor could produce a rectilinear movement directly in the inner frame (49), obviating the need for the peg (15a) and the two tracks (33, 47). The circuitry for the motor could include means to detect and indicate when the magazine has only one capsule remaining, which might set off a visual and/or audible alarm.

The motorized embodiment could be preferable if the apparatus is for use by someone who is physically enfeebled, by being unable to turn the key (7) sufficiently or unable to use a two handed device, or who is visually handicapped and unable to read the "contents" indicator (in that the control circuitry for the motor could also count the number of capsules used in that magazine).

On the other hand a rotating key (7) does not have to be the means by which such a device is operated. A rectilinear track and button in the direction of movement of the slide plate (45) and ejector plate could work equally well.

A first type of rotary magazine for use with the first inhaler embodiment of FIGS. 1 to 6 is now described with reference to FIGS. 7 to 11.

FIGS. 7 and 8 show a rotary magazine (23) formed with two main parts, a stator (103) to be held in place when loaded in an inhaler, and a rotor (107). The capsules, eight of them in this embodiment, are held in recesses (125) in the periphery of the rotating part (107), with the longitudinal axes of the capsules and recesses parallel to the axis of rotation of the rotating part (107). In FIGS. 7 and 9 it can be seen that the capsules (25) are maintained in position by pins (101). In this first magazine the capsules are already pierced during, or prior to, loading in the magazine. The pins (101), as well as maintaining the capsules in position in their recesses, also serve to plug the holes formed in the end of the capsules. These holes can exist either before the capsules are loaded into the rotary magazine (23) or may be made as the rotary magazine (23) is assembled or loaded.

FIG. 10 is an enlarged view from FIG. 8 and shows the plug, or point (105) of a pin (101) maintained within the ends of a capsule. The sealing walls (109) of the pins are formed so as to maintain a seal around the ends of the capsules, to prevent escapes of powder and, possibly more importantly, to prevent air from entering an unused capsule to contaminate it or to allow its contents to degrade. In this fashion the integrity of the capsules is maintained although they are already pierced.

Additionally it is envisaged that the magazine could be sealed into suitable outer packaging such as a sachet or blister pack to provide further protection against the environment prior to insertion into the inhaler.

FIG. 11a shows a blank position (121) in the rotary magazine (23). When a magazine is first inserted into the inhaler it is the blank position (121) which is aligned with the swirling chamber (29). The blank position, which may be an empty recess, prevents the waste of a capsule which, otherwise, would be released immediately upon insertion of the magazine.

Formed within the first type of rotary magazine (23) is a pair of capsule release cam tracks (117), one track being situated towards each end of the magazine. These cam tracks are defined, at the left hand end of FIGS. 7 and 8, by track pieces (111) and (113) and, at the right hand end, by track pieces (111) and (115). The cam tracks (117) and the track pieces (111, 113, 115) are stationary and may be formed integrally with or separately from the stator (103), depending upon the method of assembly of the magazine. The locus of the tracks is shown in FIG. 9.

The pins (101) are formed with legs (119) as followers to fit into the release cam tracks (117) between the track pieces. As the rotor (107) rotates and the pins (101) rotate with it, so the legs (119) of the pins (101) follow the cam tracks (117). The pins are formed to be axially movable within the rotor (107), that is to the left and right in FIGS. 7 and 8. FIG. 9 shows positions in the cam tracks where there are bulges (123), in both cases towards the nearest axial end of the magazine. As the pin legs (119) follow the tracks, they are caused, at the bulges (123), to move out towards the ends of the magazine. The bulges are situated at the 'use position', i.e. where a recess (125) in a magazine inserted into the inhaler is part of the swirling chamber (29) of the inhaler and a capsule in that recess is to be used. At this point, therefore, the two pins (101) holding that capsule move apart, thereby unplugging their capsule (25) and releasing it. Thus, the capsules are plugged tightly until their recesses (125) reach this 'use position' where they are released. When, after use, they are returned to their recesses by the ejector plate (17) the capsules are kept in their recesses as the magazine is rotated. As a recess (125) is rotated away from the 'use position', the legs of the pins (101) of that recess continue to follow the tracks; they come towards each other again, and re-plug the used capsule. This is useful, not only in preventing capsules from moving about freely, possibly jamming the magazine, but also in preventing any residual powder in spent capsules from escaping to contaminate the inhaler, and causing it to need further cleaning.

In the above described first rotary magazine (23), although the capsules may be pierced before loading into the magazine, the pins are so shaped that they pierce the capsules upon loading of the magazine with the capsules. Alternatively they can be shaped differently so that they merely provide a plug for pre-pierced capsules.

Figure 12:
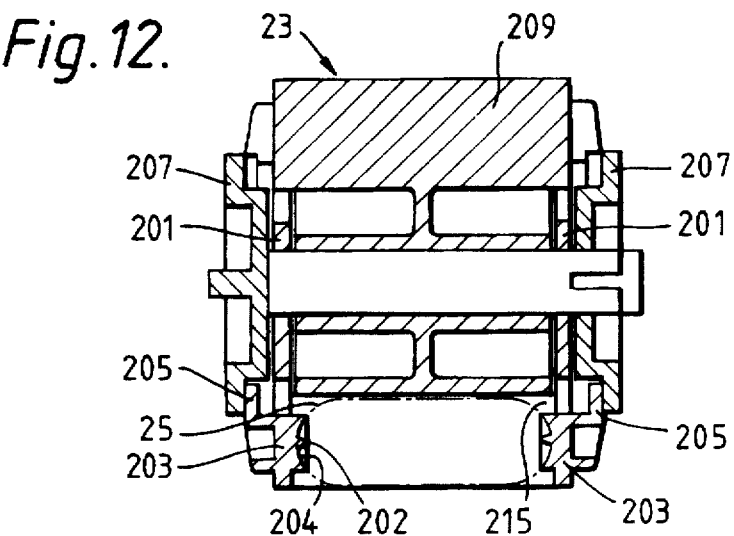
FIG. 12 is a side sectional view of a second rotary magazine embodiment according to the present invention for use in the inhaler of FIG. 1.
Figure 13:
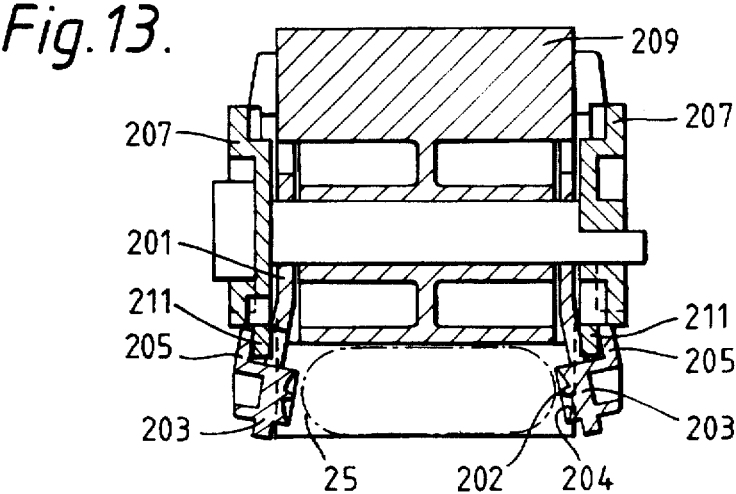
FIG. 13 is a view of the same section as FIG. 12 when the magazine has been rotated to a position where a capsule is ready for use.
Figure 14:
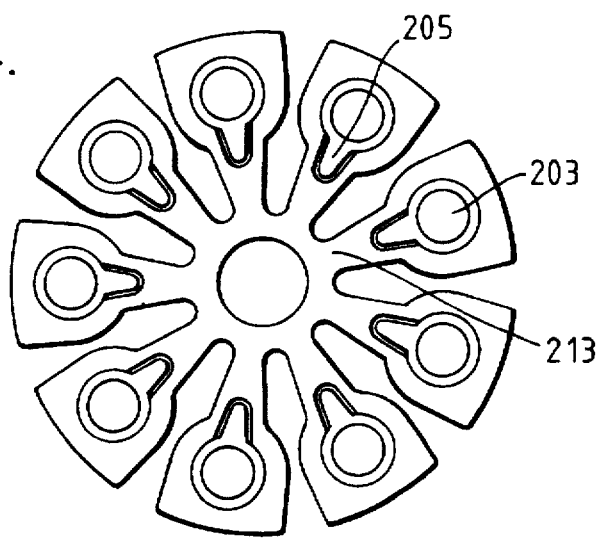
FIG. 14 is an elevational view of a daisy wheel used in the magazine of FIGS. 12 and 13.

A second type of rotary magazine also for use in the first embodiment of the inhaler is described with reference to FIGS. 12 to 14. As with previously described magazine the intention is to deliver a pierced capsule to the 'use position' and the magazine must be inserted correctly to allow this. Again, as with the first described magazine the capsules are to be pierced before a magazine is inserted into the inhaler. In this particular magazine the capsules are pierced, for example by laser, before loading into the magazine, although it is possible to use pins which only pierce the capsules as, or before, they are loaded into the magazine. This design of magazine therefore also maintains a seal on the ends of the capsules until they are required for use and after they are returned.

In this second type of magazine, there is a rotor (209) in the periphery of which are formed the recesses (215) holding the capsules (25), with the longitudinal axes of the capsules and recesses parallel to the axis of rotation of the rotor (209). It is also formed with two end pieces (207) which are stationary and two daisy wheels (201) which rotate with the rotor (209). As with the first type of magazine, the rotor rotates so each capsule is, one after the other, taken to the 'use position' where it may then be used.

The daisy wheels (201) (FIG. 14) are formed with a core section (213) and a plugging portion (203), the plugging portions each holding an end of a capsule when a magazine has been loaded. Attached to the plugging portion (203) is a raised portion (205) which is formed to be out of the plane of the rest of the daisy wheel (201) and to leave a gap in the daisy wheel along that length of the main plane running parallel to the extent of the raised portion (205). Both of the end pieces (207) on the stator of the magazine (23) have a projection (211) which exists only where the capsules are to be released at the 'use position'. The projections (211) on both sides of the magazine (23) catch the raised portions (205) of the daisy wheels as they pass. In catching the raised portions the projections move them further apart, as can be seen from FIG. 13. Because the daisy wheel is not solid beneath the extent of the raised portions (205), i.e. the raised portions (205) appear as bent tabs leaving an opening in the wheel, no other part of the daisy wheel catches on the projections (211).

Pulling the raised portions away from each other causes the plugging portions (203) of the daisy wheel also to move apart, whereby a capsule held between them is released. Normally there is a residual bias in the daisy wheels (201) to maintain a pressure of the rims (204), surrounding the plugs (202), on the capsules to keep them from falling out and also to maintain a seal on any of those capsules which may be slightly shorter than the average.

Since the projections (211) in the stationary part only exist at the 'use position' the plugging portions (203) of the daisy wheels only release the capsules when they are in the use position. Again, as in the case of the first magazine, when a capsule is returned to its original recess by the ejector plate and tab and the magazine is rotated for the next capsule to be released, the plugging portions (203) reclasp the capsules and prevent them from jamming the mechanism and releasing any residual powder. Also, as with the first type of magazine, magazines of the second type are each provided with a blank position or empty recess.

A second inhaler embodiment in accordance with the present invention will now be described with reference to FIGS. 15 to 20. In this embodiment, capsules held in rotary magazines are pierced, just before use, by pins included in the inhaler.

Figure 15:
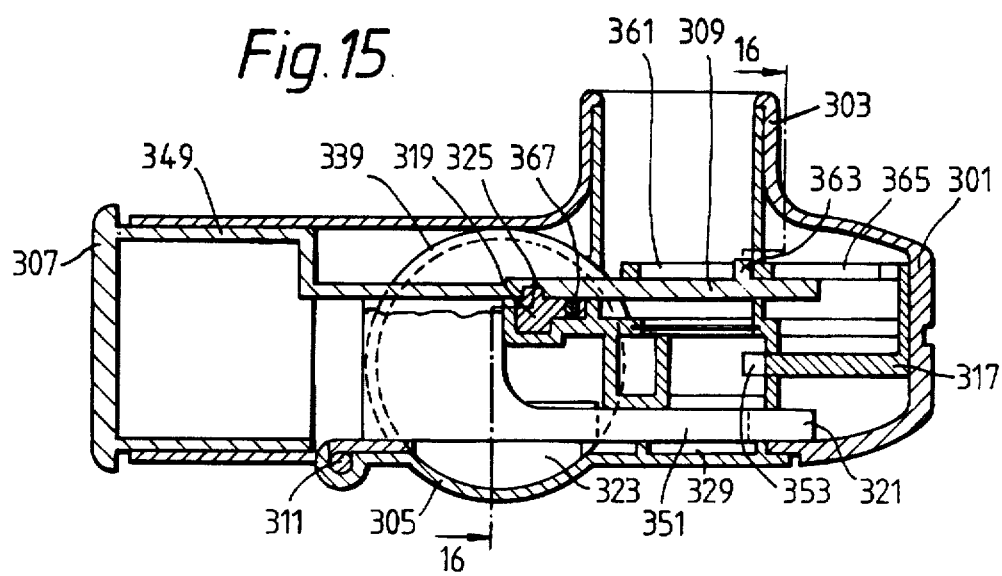
FIG. 15 is a side sectional view of a second inhaler embodiment of the present invention.
Figure 16:
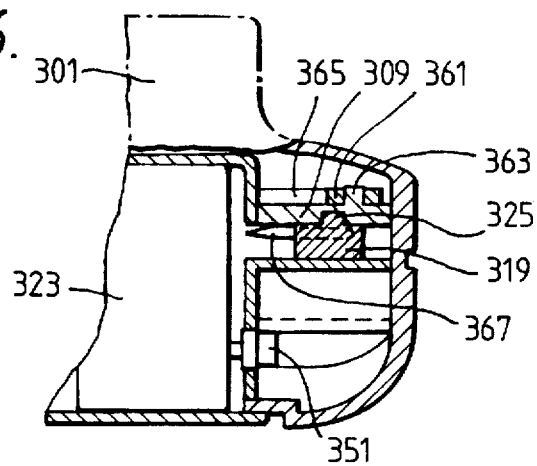
FIG. 16 is a partial sectional view taken along the line 16—16 in FIG. 15.

Referring to FIG. 15, there is shown an inhaler with a main body (301) and a mouthpiece nozzle (303) on one side of the main body towards one end of the inhaler. On the other side of the main body from the mouthpiece there is provided a rotary magazine chamber cover (305) pivoted around pivot (311) situated on the same side of the body as the magazine chamber cover (305) and towards the other end of the inhaler from the mouthpiece. By opening the cover (305) a rotary magazine (323) may be removed from or placed into a magazine chamber (339) situated roughly in the middle of the inhaler.

At an extreme end of the inhaler, away from the mouthpiece nozzle there is an operating handle (307) which is part of an operating frame (349) which extends away from the operating handle (307) to pass both sides of the rotary magazine (323) situated in the middle of the inhaler. In a motorized embodiment, a motor (307a) drives the operating frame (349). The frame (349) is configured to move back and forth within the inhaler, that is, in the orientation of FIG. 15, to the left and right. Forming part of the operating frame (349) are the operating plates (309) one of which is situated on each side of the rotary magazine (323). As will be described later the plates (309) are used to work an ejector mechanism by which a used capsule is ejected from the swirling chamber (329) from which a user inhales the contents of the capsules. The operating plates (309) also work the mechanism by which unpierced capsules, held in a loaded rotary magazine, are pierced just before use. The operating plates (309) are situated within the main body (301) of the inhaler towards the side of the main body from which the mouthpiece (303) protrudes.

A driven arm (351) forms a further part of the operating frame (349). This arm is for rotating the rotary magazine by the use of an arm protrusion (321) catching ratchet pieces formed on the side of the rotary magazine. As with the first inhaler embodiment, either the magazine itself of the magazine in combination with the magazine chamber (339) is provided with means (not shown) by which the rotary magazine is prevented from rotating in a reverse direction and possibly with means to ensure that a magazine (323) does not rotate more or less than the amount necessary for it to present one new capsule to the swirling chamber (329). It can be seen from FIG. 17 that there is only one such driven arm (351) in this embodiment, although it is possible to use two, one on each side of the rotary magazine (323).

The extraction of the medicament through the use of the swirling chamber will be described in detail later. However, in brief, a pierced capsule is presented, from a loaded magazine, into the swirling chamber (329). By inhaling through the mouthpiece, a user draws air in through the two air inlets (314) causing the powder in the capsule to leave the capsule, and to exit the swirling chamber passing out through the mesh (337) and the mouthpiece (303). The rotary magazine holds capsules in recesses (341) whose longitudinal axes are parallel to the axis of rotation of the magazine and which deliver the capsules, sideways on, to the chamber (329) from a chordal position, one at a time. A recess, in reaching the use position and delivering a capsule for use, forms part of the swirling chamber (329) and faces away from the middle of the inhaler and not towards the middle as in the first embodiment, since the magazine in this embodiment is placed in the middle of the device.

A capsule ejector plate (317) is also provided within the inhaler. This has an end tab (353) and is sealed and works in a similar fashion to the ejector plate and end tab of the first embodiment, that is the end tab (353) forms part of the side wall of the swirling chamber and is movable across the diameter of the chamber towards the recess (341). However, in this second inhaler embodiment the ejector plate is advanced via lost motion connections, seen clearly in FIG. 18, which include lost motion pins (363) attached to the operating plates (309), on both sides of the rotary magazine, and lost motion connectors (361).

Figure 19A:
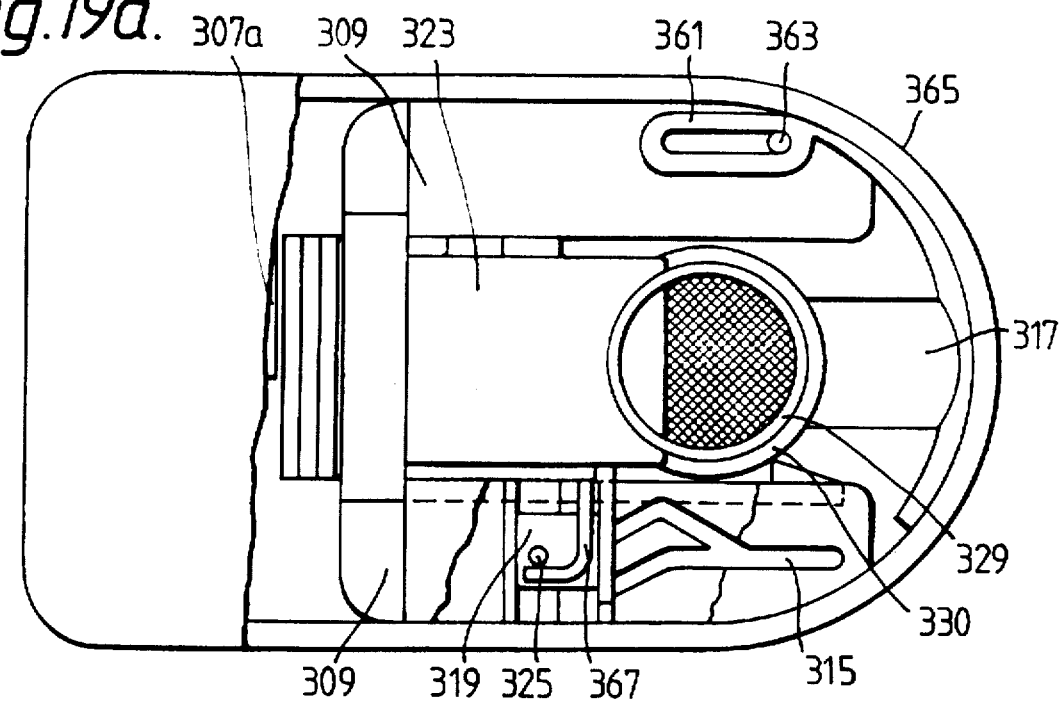
FIG. 19a is a top view of the motorized inhaler of FIG. 15a looking at various sections through the depth of the inhaler.

There is also provided a cam track (315) as part of each operating plate (309) as can be seen in FIGS. 19 and 20. Into each cam track (315) slots a protrusion (325) which is part of a pin-holding piece (319) also provided on each side of the magazine. Each pin-holding piece (319) contains pins (367) for piercing capsules and is movable, in the orientation of FIG. 16, to the left and right, that is towards and away from the rotary magazine (323). The pins (367), moving with the pin-holding pieces (319), pierce the ends of capsules held in the rotary magazine.

The operation of the mechanism to pierce capsules, to eject used capsules, and to replace them with new ones will now be described especially with reference to FIGS. 15, 18, 19 and 20.

Figure 15A:
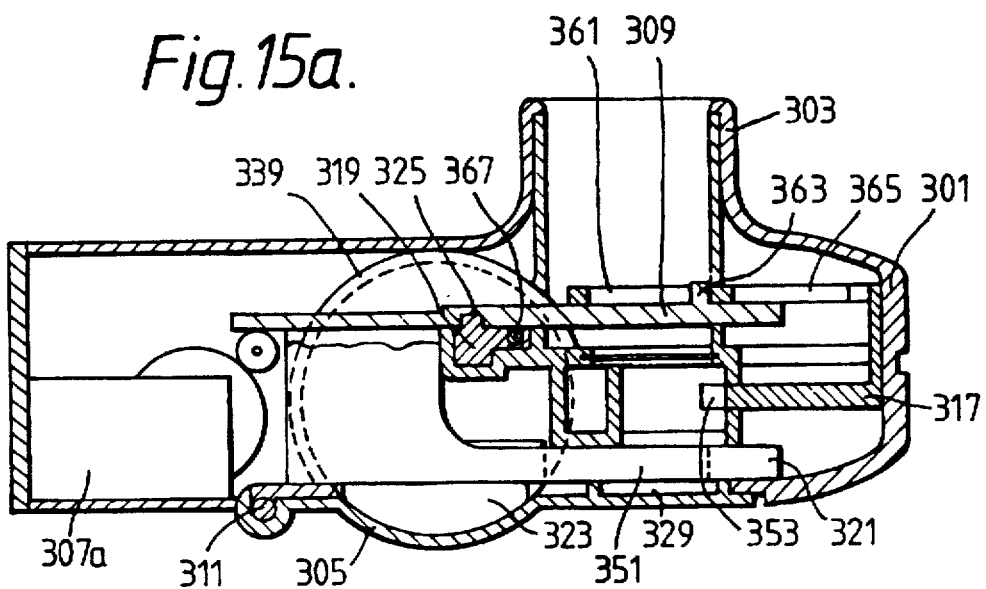
FIG. 15a is a side sectional view of a motorized variant of the second inhaler embodiment of the present invention.
Figure 17A:
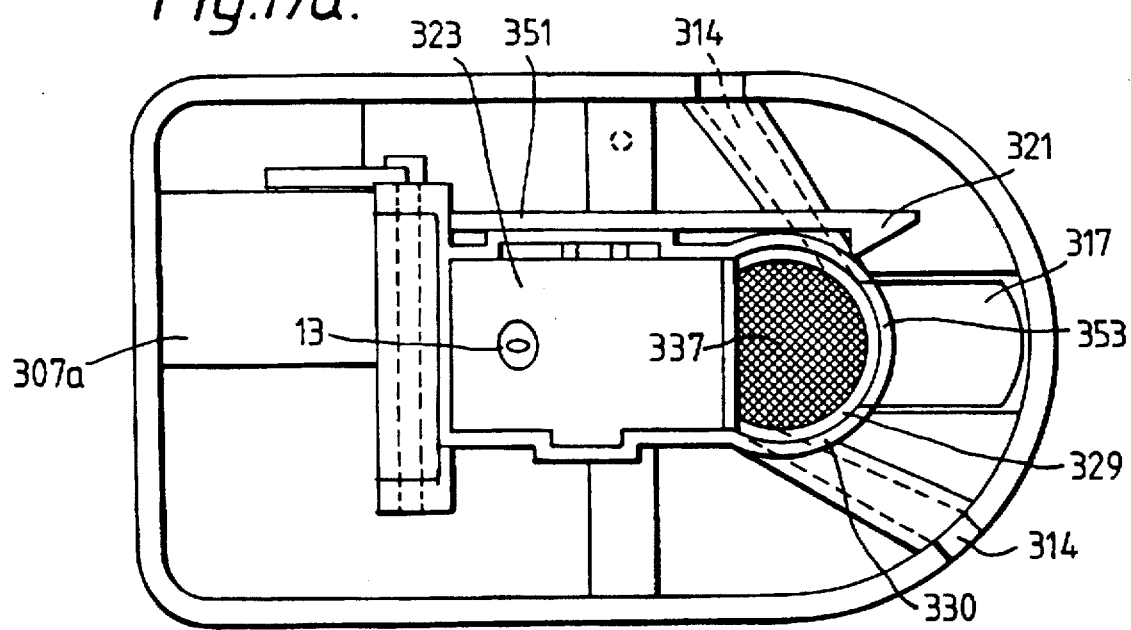
FIG. 17a is an underneath plan view of the motorized inhaler of FIG. 15a with the outer cover removed.
Figure 18A:
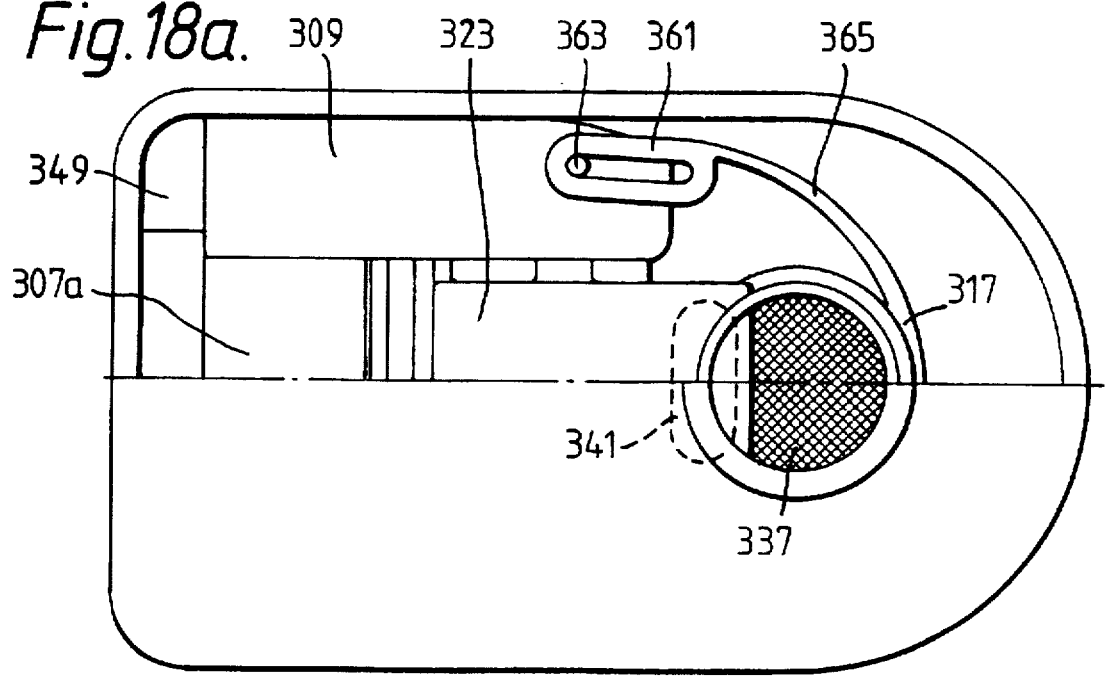
FIG. 18a is a split view showing in one half a top plan view of FIG. 15a and in the other a top plan view of the motorized inhaler of FIG. 15a part way through the 'use cycle' with the top cover removed.

As can be seen in FIG. 18 the operating handle (307) may be pulled out to an extended position. As the handle is withdrawn from the main body (301), so the whole operating frame (349), shown in other Figures, including the operating plates (309) and the driven arm (351) is also moved in the same direction.

Where motorized, when the motor (307a) is operated, it moves the operating frame (349) in a rectilinear direction from left to right in FIG. 15a, using a series of gears or other means, which includes the operating plates (309) and the driven arm (351).

The lost motion pins (363) move with the operating plates and run in tracks formed in the lost motion connectors (361). As each protrusion is drawn along its track it eventually meets the end of the track and contacts the lost motion connector (361) which causes the connector (361) to move in the same direction. The lost motion connectors (361) are integral with the ejector plate (317) and draw the ejector plate with them, also in the same direction. Thus, when the handle is drawn out of the main body (or when the motor is operated) this draws with it the operating plate (309), the lost motion pins (363), the lost motion connectors (361), and the ejector plate (317) in the same direction. Through this a capsule in the swirling chamber (329) is ejected into its recess (341) in the rotary magazine (323), by the end tab (353) of the ejector plate (317).

The end tab of the ejector plate (317) will arrive at the limit of its movement as it meets the rotary magazine (323). Preferably there is provided a stop to prevent the end tab (353) from impinging upon the rotary movement of the rotary magazine (323) whilst, at the same time, not preventing the end tab from keeping a capsule within its recess.

After the ejector plate (317) has come to the limit of its movement the operating handle (307) may still be drawn further from the main body (or the motor (307a) continues to operate to draw the frame along) and the ejector plate (317) does not prevent this. The lost motion connectors (361) are connected to the ejector plate (317) through an arcuate and flexible piece (365). When it is in its rest position this flexible piece forms a shape which follows the inner surface of the main body (301) which, as shown in FIG. 19, describes the major part of a semi-circle. However, when the ejector plate (317) has reached the limit of its movement, in FIG. 18, the flexible piece (365) on both sides of the ejector plate (317) is straightened slightly by the further movement of the operating plates (309). Since the lost motion pins (363) on the operating plates (309) are circular the lost motion connectors (361) rotate about them.

When the operating handle (307) is pushed back in towards the inhaler this initially reduces the tension on the flexible pieces (365) to return them to their original shape.

In a motorized embodiment, when the operating frame reaches the limit of its movement, this is detected by the motor control circuit, which reverses the motor and moves the operating frame (349) from left to right to accomplish the same thing.

At first the ejector plate remains stationary whilst the lost motion pins (363) move up along the track of the lost motion connector (361). It is not until the pins (363) reach the other end of the tracks that they push the ejector plate (317) away from the rotary magazine to its rest position, where the end tab (353) forms part of the peripheral wall of the swirling chamber (329).

Describing now the piercing of capsules by the pins (367) held on either side of the rotary magazine (323), this also is achieved through the withdrawal of the handle (307) (or operation of the motor (307a)) and using the cam tracks (315). As the handle (307) is drawn out from the inhaler (or the motor moves the frame (349)), the pin-holding protrusions (325) which are cam track followers remain in the same longitudinal position within the inhaler. The walls of the cam tracks (315) passing along the length of the inhaler with the operating plates (309) do, however, force each follower (325) to follow the wall contours and move laterally.

Specifically, with reference to FIG. 20, as the handle is initially withdrawn from the main body (or the motor is operated), each cam follower protrusion moves from left to right until it encounters a fork in the came track. However, the follower protrusion (325) will follow the path offering least resistance, and thus, in this case, it maintains its lateral position. The follower (325) maintains this position until it reaches point 'A' in FIG. 20. Here the cam track turns to one side, causing the follower (325) also to move to one side, which in this case is towards the centre of the inhaler and the rotary magazine. The cam rack of FIG. 20 is mirrored on the other side of the rotary magazine (323) and at this point the other track will also cause its follower to move inwards towards the rotary magazine. As the follower (325) is forced to move inwards so is the pin-holding piece (319) and the pin (367). As the cam track heads towards the centre of the inhaler the pin on each side of the rotary magazine passes through a respective hold in the side of the magazine and pierces an end of the capsule currently in the pinning position within the rotary magazine. In this described example the pinning position is not the same as the use position but immediately precedes it. At the point 'B' in FIG. 20 the cam tracks and followers (325) have reached the limits of their lateral movement towards the rotary magazine and the track (315) turns back out towards the sides of the inhaler until the follower reaches position 'C' when the track runs straight again. The follower is therefore withdrawn from the rotary magazine which is then free to rotate again.

Once the pins are free from the rotary magazine the driven arm (351) indexes the rotary magazine (323) through one position and the newly pierced capsule replaces the one which has just been ejected by the ejector plate (317). Thus the user is presented with a freshly pierced capsule which is used as described later. In this particular example, magazine indexing rotation begins when each follower (325) has reached position 'C' and finishes when the limit of the movement of the handle is reached and each follower (325) reaches position 'D'.

Once position 'D' has been reached and the handle (307) is released, then elastic forces caused by the flexing of the flexible pieces (365) will start to move the handle back in the direction of the main body, which action is completed by the user pushing the handle the rest of the way back in. Alternatively there may be a spring to achieve the whole of the handle return process. During the return of the handle back into the main body the follower passes back through position 'C'. Beyond this point there is no longer any elastic force from the flexible pieces (365) so the lost motion pins (363) of the operating plates (309) pass along the tracks of the lost motion connectors (361). On the return journey too the came track followers follow the paths of least resistance and therefore do not pass back through position 'B' but continue in their same lateral position until forced to move further outwards by the cam track and back in again to their original positions. The extent to which the track bulges on its return is not important, provided at the start of the ejection, pinning, and magazine rotation process a follower does not allow the wrong track.

This second inhaler embodiment also envisages having a window in the magazine chamber cover, or possibly on the other side of the inhaler, whereby an indication of the number of capsules used or remaining in a magazine can easily be ascertained by the user.

In the second embodiment of inhaler any means which produces rectilinear movement in the operating frame (349) will work the apparatus. This includes the arcuate and rectilinear track mechanisms used in the first described embodiment of inhaler.

A third rotary magazine embodiment for use in this second embodiment of inhaler is now described with reference to FIGS. 21 to 24. This third magazine (323) comprises a stator (401) and a rotor or carousel (405). The carousel (405) has a number of longitudinal recesses (417) in its periphery, parallel to its axis of rotation, for holding capsules. The stator (401) includes a peripheral wall (407) which is provided to prevent any capsules from escaping from the magazine except at the 'use position' where a gap (403) is provided in the wall. The peripheral wall may be solid or may have gaps, provided the gaps do not cause capsules to jam or allow them to escape. Also, somewhere within the peripheral wall there is provided a window (409) through which numbers written or otherwise placed on the carousel (405), between the recesses, may be viewed to ascertain how many capsules have, or have not, been used.

As can be seen from FIG. 24 the capsules are simply kept within the rotating carousel (405) and are prevented from escaping only by the peripheral wall (407) of the stator (401) of the magazine. It can also be seen that there is a blank position where no capsule is to be found. When a magazine is first mounted into the device this blank position is to be put in the use position to prevent the wastage of a capsule, as with the magazines of the first embodiment. FIG. 23 shows that the magazine is provided with a key-way (411) for ensuring that it is orientated in the correct position within the magazine chamber. The magazines can instead be made in such a way that they may be used either way round, so long as the gap (403) in the peripheral wall (407) is situated at the correct position on insertion, whereby the recesses (417) in the carousel can be used to form the recess part (341) of the swirling chamber (329).

FIG. 23 also shows a piercing hold (413) formed in the side wall of the stator (401) of the magazine. One of the pins (367) in the inhaler passes through this hole to puncture the adjacent end of the capsule as the capsules pass, one by one, through the piercing position, before use.

The other side face of the magazine is attached to the carousel. This second side face (415) can be rotatable with the carousel (405), with pin holes provided in the face (415) at each recess, to allow the pin on that side of the inhaler to pass through the face (415) into the rotary magazine to pierce the second ends of the capsules. Alternatively the end face (415) may be stationary, with one pin hole opposing that on the face belonging to the magazine stator. When the inhaler mechanism is operated a spent capsule is ejected from the swirling chamber at the same time as the next capsule is pierced. The freshly pierced capsule is then rotated to the gap (403) in the peripheral wall (407) and is free to leave the magazine.

A third embodiment of the inhaler of the invention will now be described by reference to FIGS. 25–31.

There is a front cover (566) from one face of which protrudes a mouthpiece nozzle (503) through which medicament held in capsules is drawn out and delivered to a user. This takes place in a swirling chamber (529) in the rear cover (565) in a capsule-emptying phase.

Figure 25:
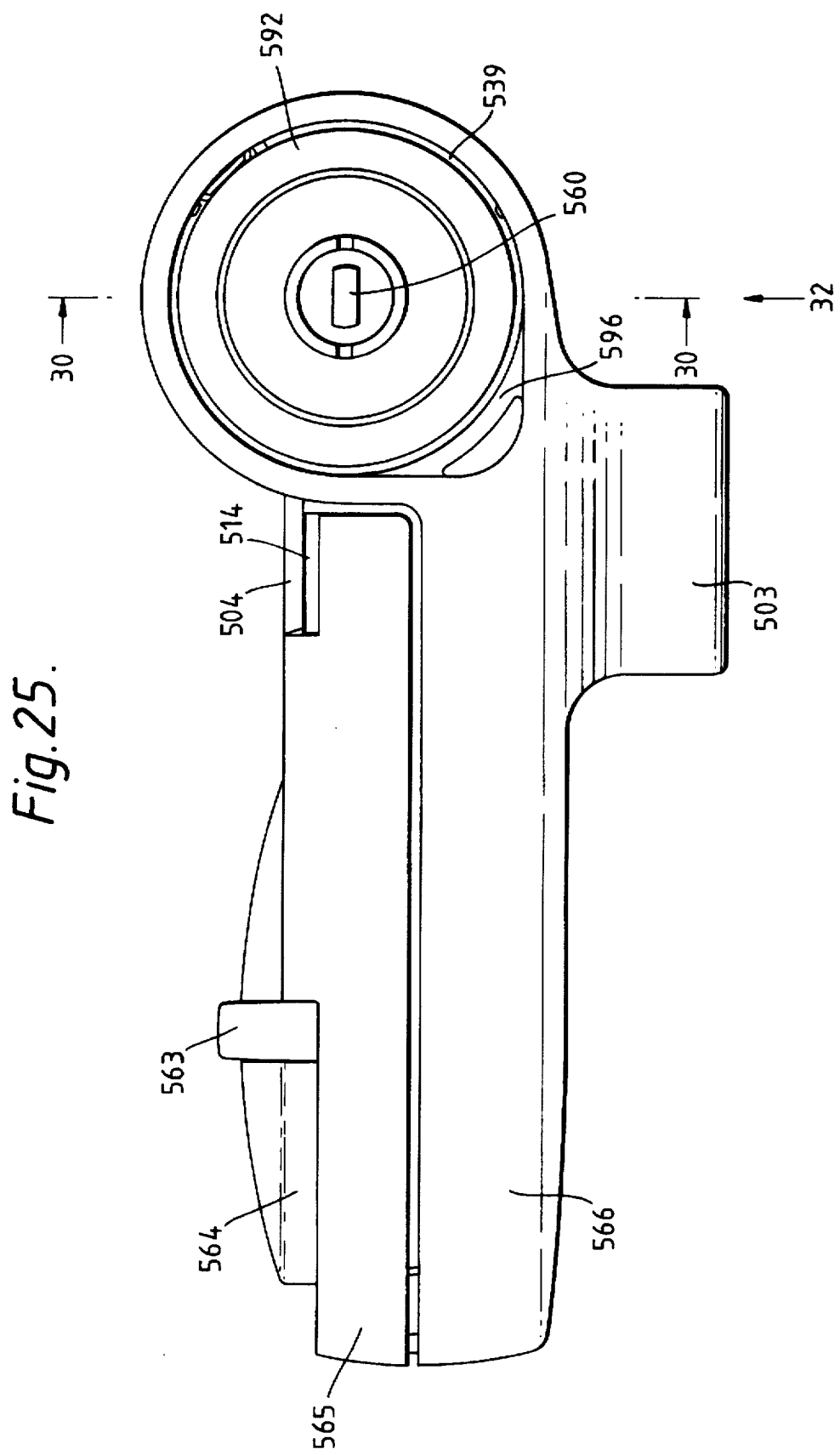
FIG. 25 is a side elevational view of a third embodiment of inhaler in accordance with the present invention.
Figure 26:
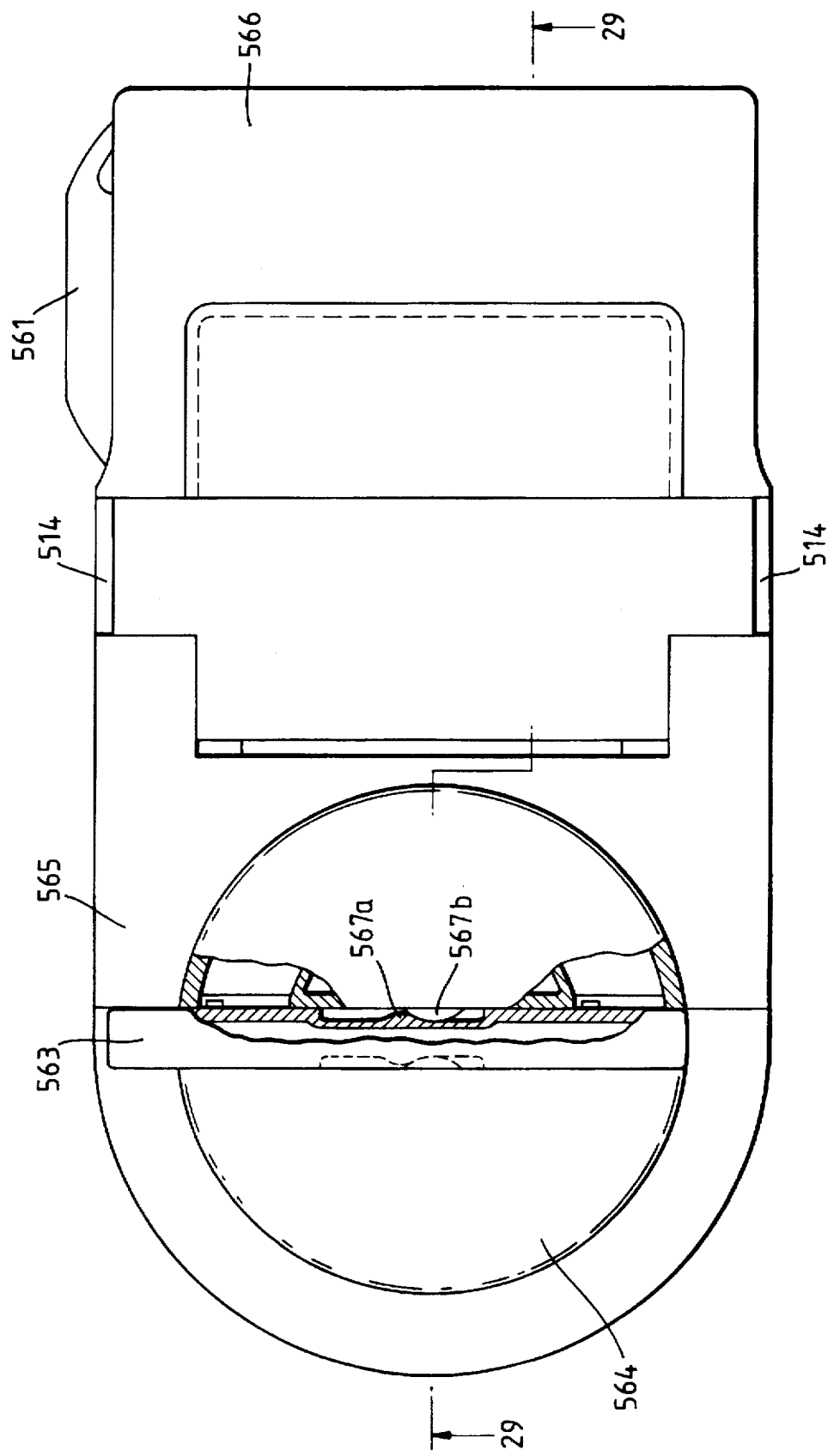
FIG. 26 is a top plan view of the inhaler shown in FIG. 25.
Figure 27:
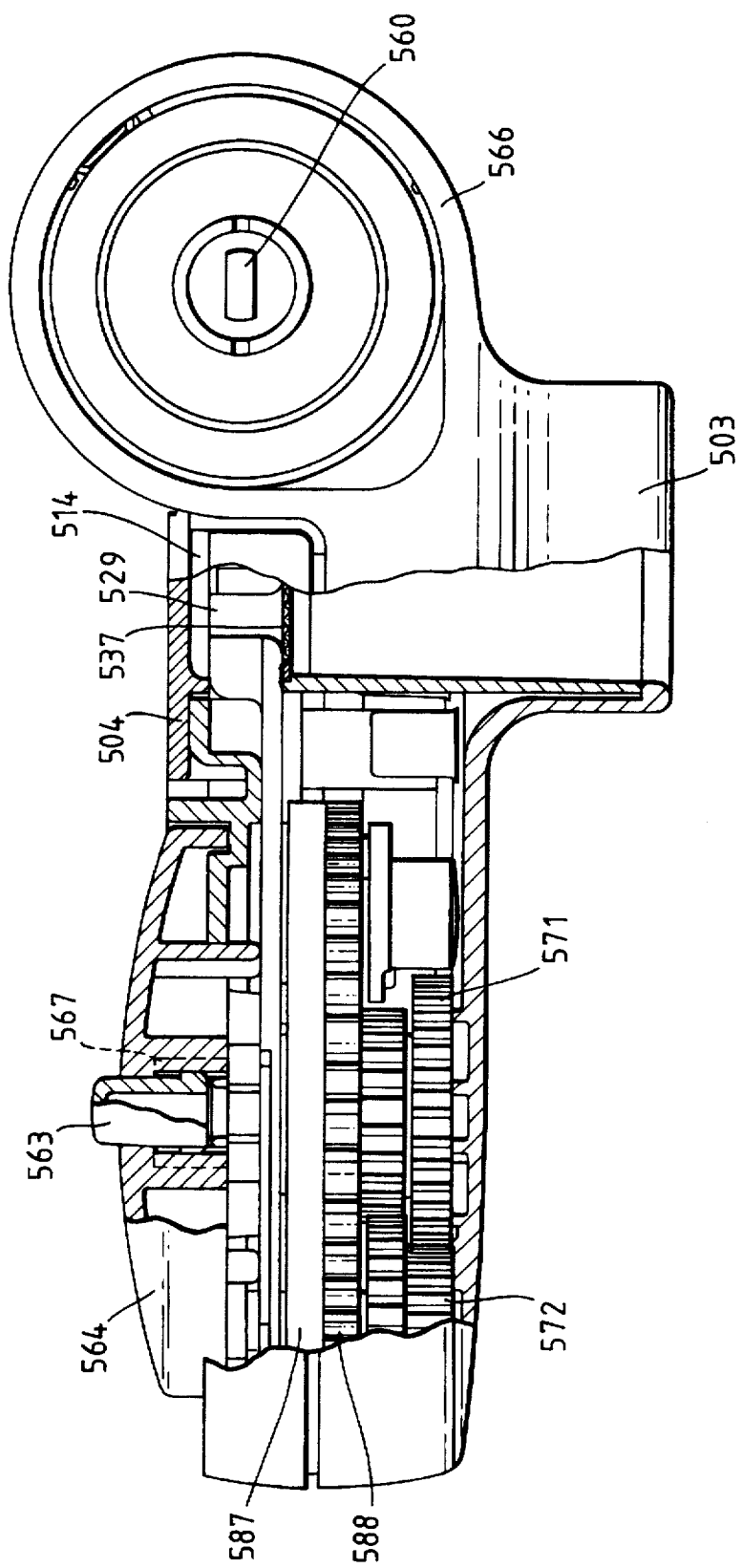
FIG. 27 is a partly sectioned side view, corresponding to FIG. 25, and showing the third embodiment of inhaler.
Figure 30:
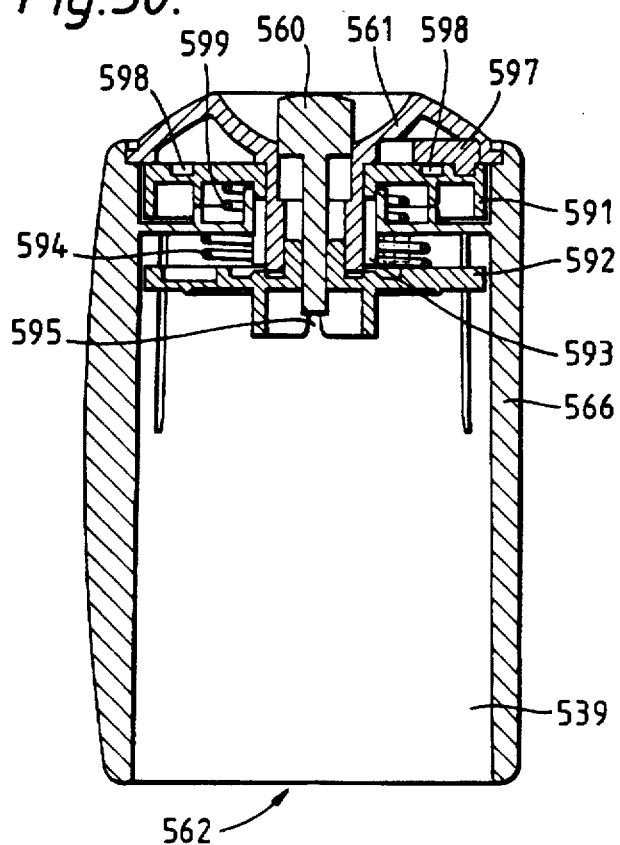
FIG. 30 is a sectional view taken on the line 30—30 of FIG. 25.
Figure 31:
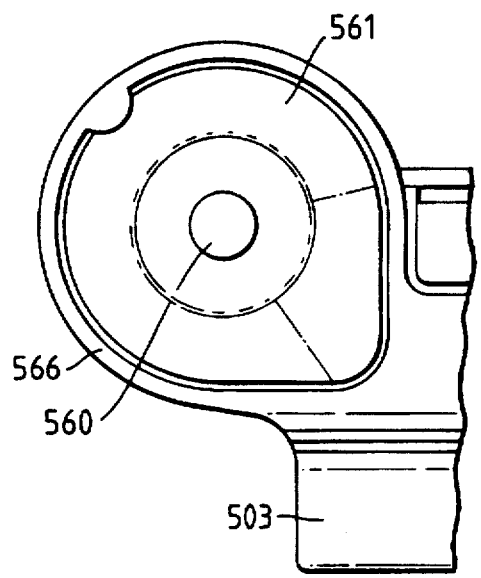
FIG. 31 is a partial elevation of the magazine housing when viewed from the rear of FIG. 25.

FIG. 31 shows a part side view indicating an end cap (561) through which a magazine ejector button (560) protrudes. When the magazine ejector button is depressed the used magazine of spent medicament capsules is ejected through aperture (562) (FIG. 30) in the side of the front cover (566) (FIG. 25). Also accessible from the outside is a slider (563) mounted diametrically of the wheel (564) and which, when moved along its receiving slot diametrically across the wheel (564) by its full extent, may then be used to rotate the wheel through a maximum angle of 180° about a vertical axis (8). Turning this wheel (564) about the vertical axis (8) operates the mechanism of the inhaler to eject a spent capsule from the swirling chamber (529) shown in FIG. 28, and to replace it with an unused capsule from the magazine for the operator to use.

Two air inlet passages (514) (FIG. 28) open into the sides of the rear cover (565) as shown in FIG. 25. When the user inhales through the mouthpiece nozzle (503) air is drawn through these inlet passages (514) into the swirling chamber (529) where it picks up the contents of a capsule and exhausts them through a mesh (537) and the nozzle (503).

Figure 28:
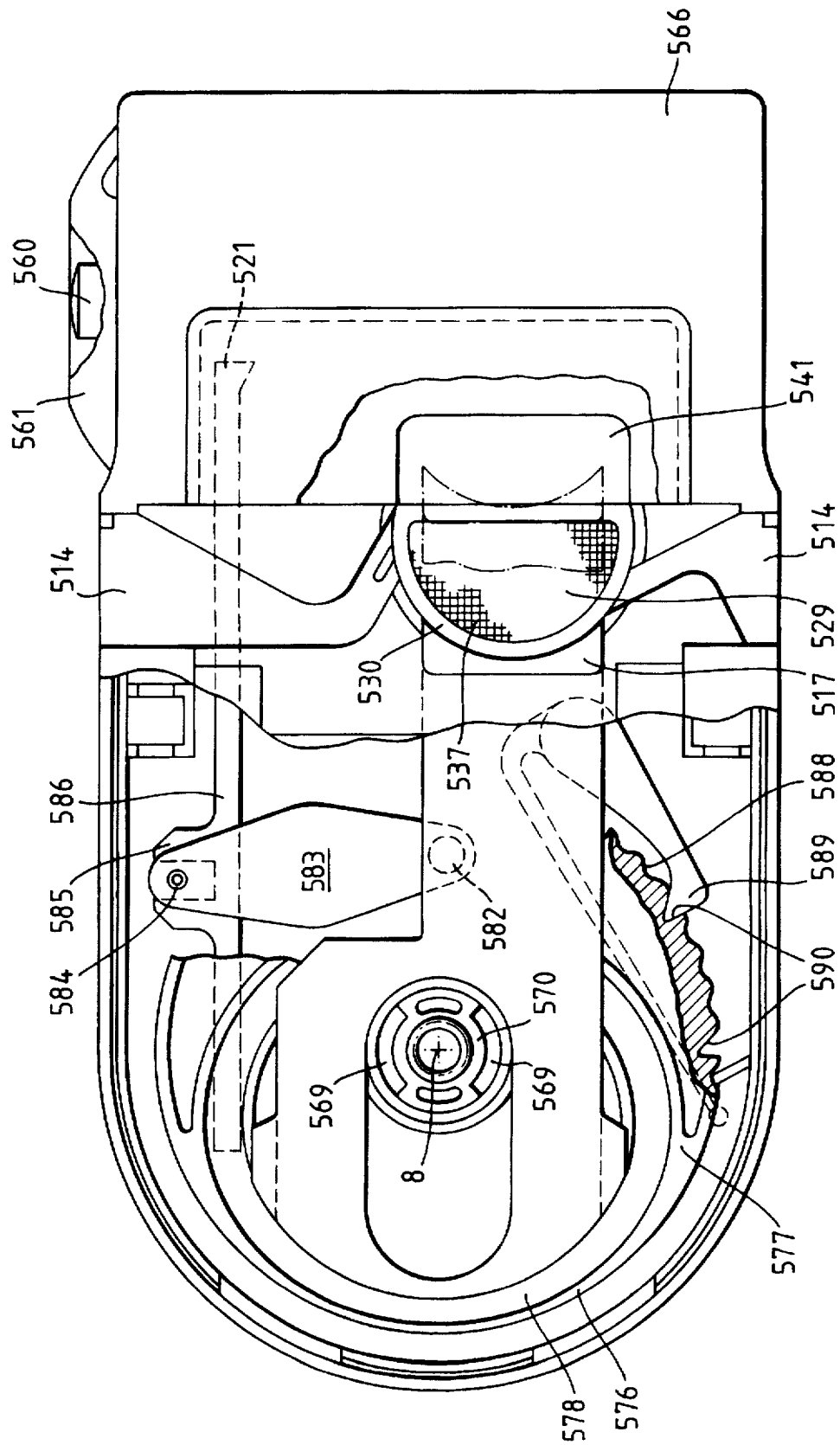
FIG. 28 is a partially sectioned top view of the inhaler of FIGS. 25 to 27.

A capsule is trapped in the swirling chamber defined by a mesh (537) below it, by a door (504) above it and by the peripheral side wall (530) (FIG. 28). In its open position the door (504) enables the chamber to be accessed for cleaning and in its closed position functions as the further chamber wall constraining the capsule and also completes the air inlet passages (514). The door (504) may be provided with air holes to augment or replace the open ends of the inlet passages (514) so that air may be drawn into the chamber through its sides, rear or both.

Figure 32:
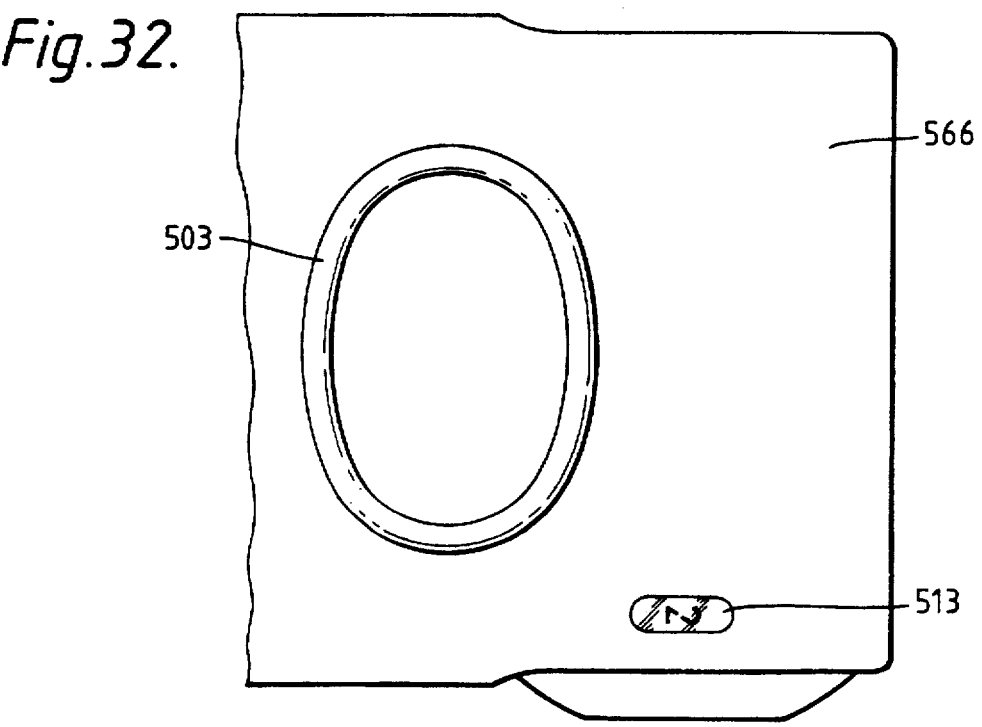
FIG. 32 is a partial elevation of the magazine housing when viewed along the direction of arrow 32 in FIG. 25.

FIG. 32 shows a front view of the inhaler of FIG. 25. There is a window (513) mounted in the front cover (566) through which can be seen a number representing the number of unused, or alternatively spent, capsules within the loaded rotary magazine.

The operation of this inhaler, whereby a capsule which has been used and is left in the swirling chamber (529) is removed and replaced by an unused capsule from the rotary magazine, will be described with reference to FIGS. 25–32.

Figure 29:
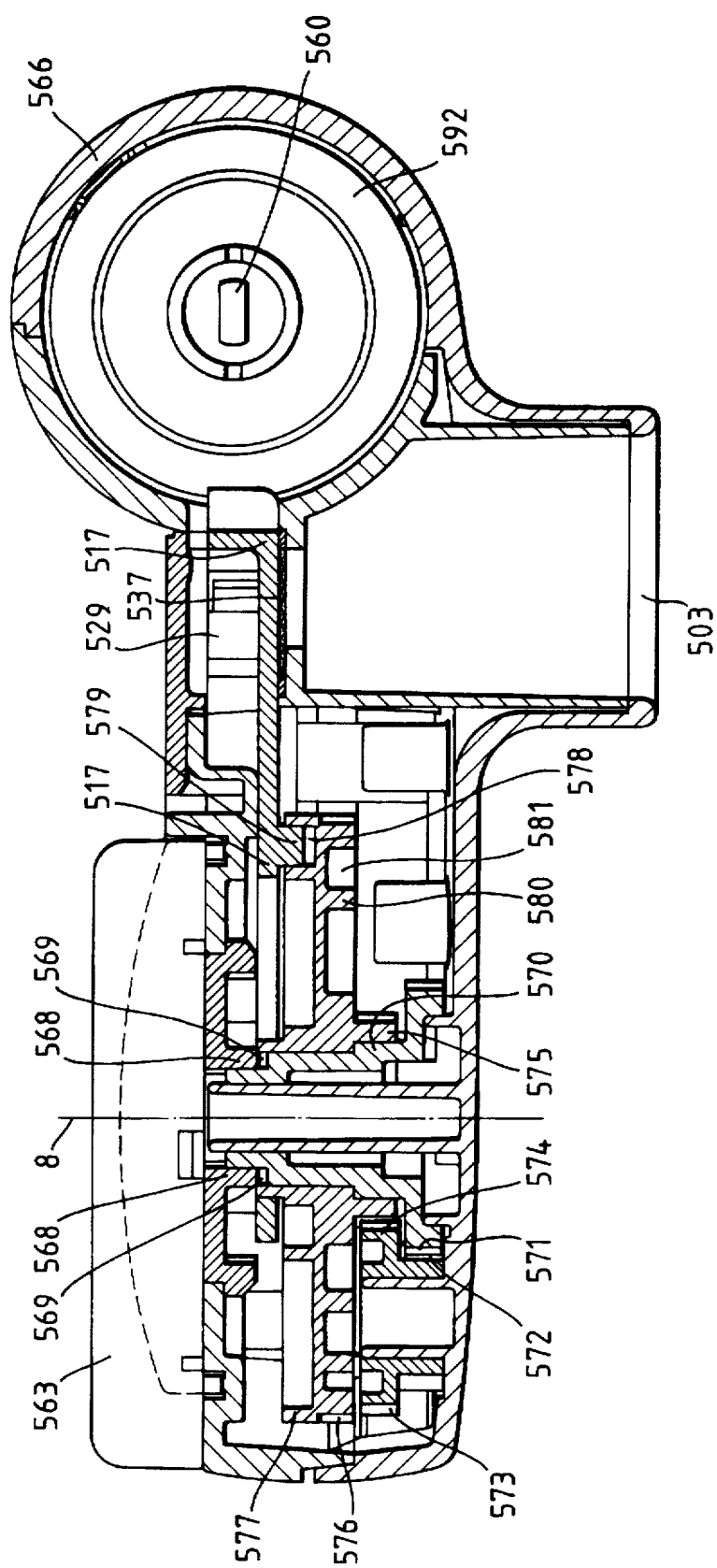
FIG. 29 is a sectional view of the inhaler of FIGS. 25 to 28, taken on the line 29—29 of FIG. 26.

When the operator wishes to use the inhaler he pushes the slider (563) diametrically across the wheel (564) to its full extent, overcoming detents formed by a rib (567a) on the slider (563) which rides over a rib (567b) on the wheel (564), and rotates the wheel and slider assembly clockwise until the slider hits a stop formed by the rear cover (565) resulting in a limit of 180° of movement about vertical axis (8). Formed as part of the wheel (564) are drive dogs (568) which, as shown in FIG. 29, protrude into the inhaler through the rear cover (565). These drive dogs (568) locate precisely with recesses (569) in a spindle (570) and cause the spindle (570) also to rotate clockwise through 180°. Integral with this spindle (570) is a gear (571) meshing with a gear (572) which forms one part of the compound gear unit (573). The second gear (574) of the compound gear unit (573) meshes with a gear (574) which is part of a cam plate (576).

The cam plate (576) comprises three functional surfaces (577, 580 and 587).

The first functional surface (577) in the upper face of the cam plate (576) has a continuous cam track recess (578) which when rotated transfers linear movement to the captive cam follower (579) attached to the ejector plate (517) causing the ejector plate (517) to move forwards and backwards across the swirling chamber (529).

The second functional surface (580) in the underside of the cam plate also has a continuous cam track recess (581) which when rotated transfers movement to a captive cam follower peg (582) (FIG. 28) attached to a rocker arm (583). When actuated to rocker arm (583) oscillates by symmetrically pivoting about its centre; it has attached to each end one of two diametrically opposite pegs (582 and 584). The peg (584) fits in a yoke (585) which forms part of the indexing rod (586). Thus, when the cam follower peg (582) is caused to move, the rotation of rocker arm (583) is transferred to linear action of the indexing rod (586). The indexing rod (586) has attached to its end a claw (521) for causing the rotary indexing of the magazine drive mechanism.

The third, circumferential, functional surface (587) (FIG. 27) of the cam plate (576) (FIG. 29) has for the majority of its length an even pattern of relief (588) which when acted upon by an integrally sprung pawl (589) (FIG. 28) creates an audible sound as confirmation of operation throughout the length of the circumferential surfaces (587), the pattern of relief (588) is interrupted by a number of local recesses (590) each of which as a shape compatible with the nose of the pawl (589) such as to prevent reverse rotation of the cam plate (576) once the ratchet nose is in the recess (590). The degree of rotation of the cam plate (576) relative to the rotation of the slider (563) is a function of the gear ratio selected and may be chosen by suitable gear ratios found to be advantageous in use.

FIGS. 30 and 31 show the end cap (561) at the opposite end to the magazine loading aperture (562). The end cap (561) has mounted on it a numbering wheel (591) which is driven by an indexing wheel (592) through castellated drive dogs (593). The indexing wheel (592) is driven by engagement with the claw (521) of the reciprocable indexing rod (586). Axial movement of the indexing wheel (592), against the compression spring (594), is allowed by virtue of the castellated drive dogs (593).

Figure 36:
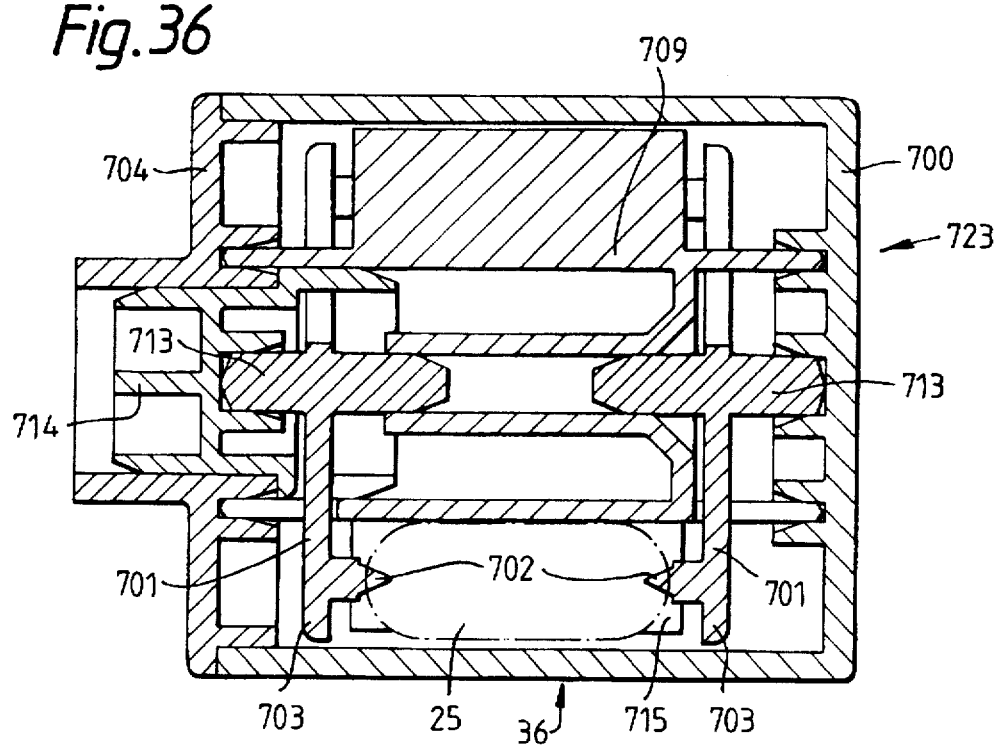
FIG. 36 is a longitudinal section taken through a fifth embodiment of the capsule magazine in accordance with the present invention.
Figure 37:
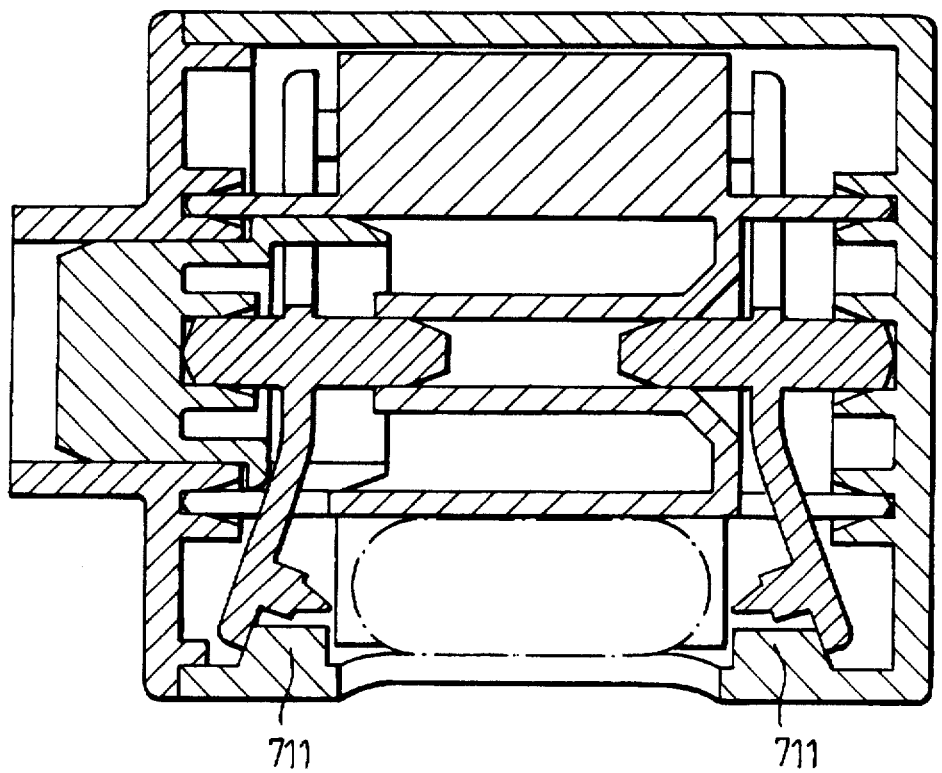
FIG. 37 is a sectional view of the magazine of FIG. 35 but viewed along the direction of arrow 36 of FIG. 35.
Figure 38:
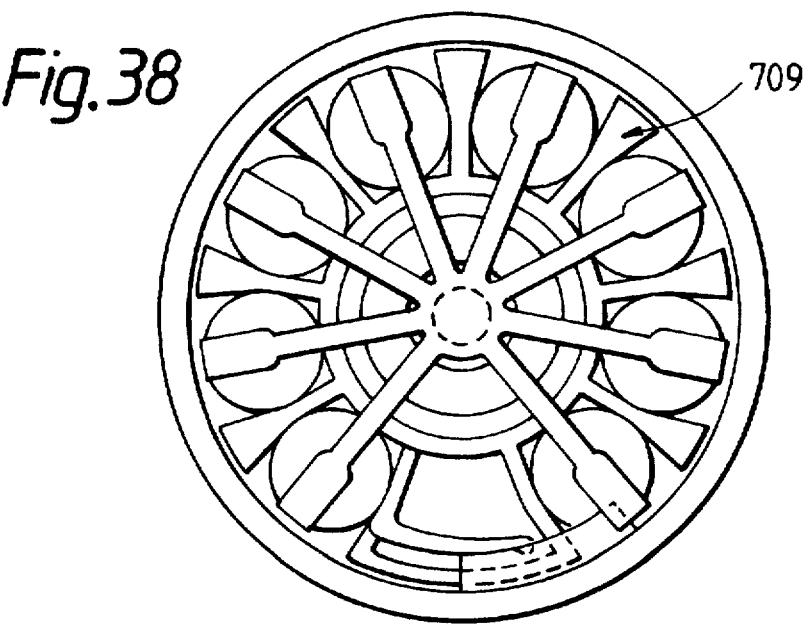
FIG. 38 is a view of the magazine of FIG. 35 when viewed from the left hand side and with the end cap 34 removed.

The magazine (623 shown in FIGS. 33 to 35, or 723 shown in FIGS. 36 to 38) is loaded through an aperture (562) of the inhaler front cover (566) with the drive blade (614, 714) on the magazine innermost. The drive blade (614 or 714) locates in the slot of the indexing wheel (595) at which time resistance will be felt as the magazine depresses the indexing wheel against its compression spring (594). The final travel of loading the magazine causes it to be retained by a catch detail created by a dimple (600) on the outer casing (636) (FIG. 33) of the magazine and an internal wall on the front cover which supports an integrally moulded spring strap (596) (FIG. 25). As the magazine (623 or 723) is inserted, the indexing wheel (592) is pressed against the compression spring (594) to a position which allows the forward motion of the claw (521) on the indexing rod (586) (FIG. 28) to rotate the indexing wheel (592) in an anticlockwise direction resulting in the central hub (631 shown in FIG. 33, or 709 in FIG. 35) of the magazine to be indexed rotationally to the next capsule station.

During the indexing stages of the magazine, a cam follower (597) (FIG. 30) mounted in the end cap (561) travels perpendicular to the axis of the end cap within a 360° arc involute cam recess (598) on the numbering wheel (591). This involute cam recess has stopped ends which act as limiters and restrict the travel to one revolution of the central hub of the magazine (631) (FIG. 33) to avoid re-use of capsules. Provided the capsule ejector plate is withdrawn from the magazine the magazine ejector button (560) can be depressed, thereby overcoming the spring strap (596), to eject the spent magazine. Preferably this is effected after one revolution of the magazine, corresponding to use of all eight capsules. The rewind torsion spring (599) can then return the numbering wheel to the initial position ready for reloading with a new magazine, because the claw (521) no longer engages the indexing wheel (592).

A fourth embodiment of a rotary magazine, to be used with the inhaler of the third embodiment is now described with reference to FIGS. 33 to 35.

Figure 35:
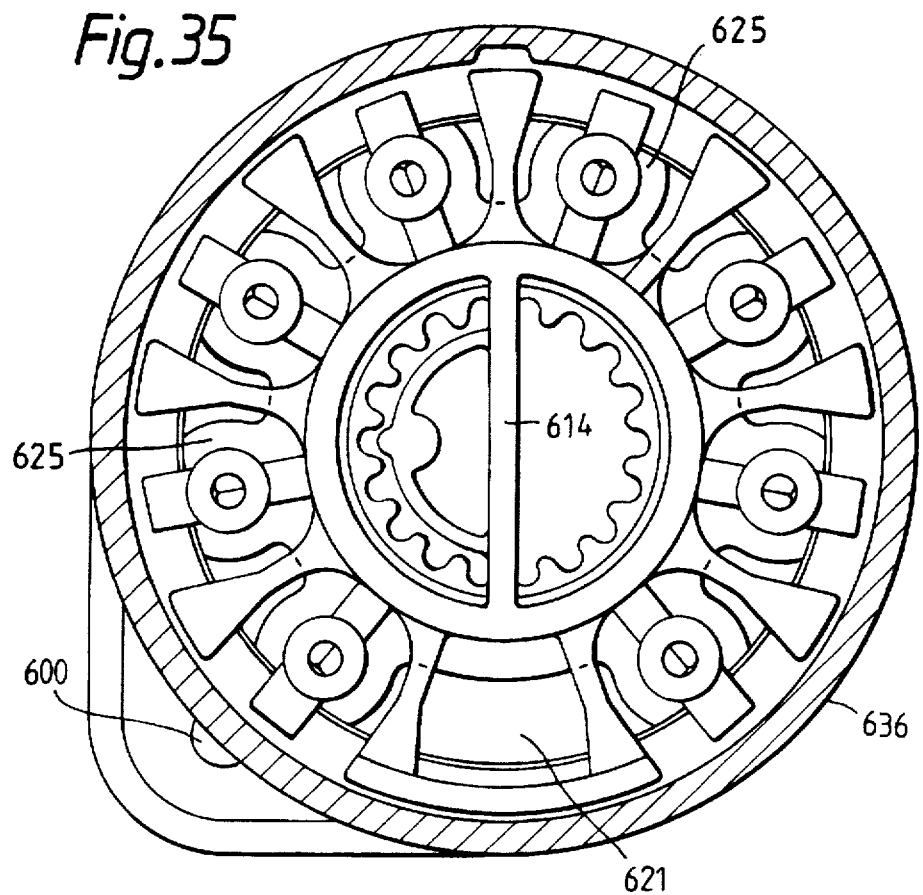
FIG. 35 is an end view of the magazine shown in FIGS. 33 and 34.

FIGS. 33 to 35 show a rotary magazine (623) formed with two main parts, a stationary part consisting of end cap (633) and outer casing (636) to be held in place when loaded in an inhaler and a rotor consisting of two end hubs (632) integrally fixed to a central hub (631).

The capsules, eight of them in the drawings, are held in recesses (625) in the periphery of the rotor central hub (631) with the longitudinal axis of the capsules and recesses parallel to the axis of rotation of the rotor assembly (631, 632). The rotor comprises the central hub (631) between two end hubs (632) fixed thereto. In FIG. 34 it can be seen that the capsules (25) are maintained in position by tips (601) of pins (605).

In this fourth embodiment of magazine the capsules are already pierced during or prior to loading in the magazine. The pins (601), as well as maintaining the capsules in position in their recesses, also serve to plug the holes formed in the ends of the capsules. These holes can exist either before the capsules are loaded into the rotary magazine (623) or may be made as the rotary magazine (623) is assembled or loaded.

FIG. 34 is an enlarged view from FIG. 33 and shows the plug, or tip (605) of a pin (601), maintained within the ends of a capsule. The sealing means (609), for example a fillet radius (606) at the base of the pin (601), are formed so as to maintain a seal around the ends of the capsules, to prevent escape of powder and, possibly more importantly, to prevent air from entering an unused capsule to contaminate it or to allow its contents to degrade. In this fashion the integrity of the capsules is maintained although they are already pierced.

Additionally, it is envisaged that when fresh the magazine could be sealed into suitable outer packaging such as a sachet or blister pack to provide further protection against the environment prior to insertion into the inhaler.

As in the case of FIG. 11a there is a blank position (621) in the rotary magazine. The blank position, which may be an empty recess, prevents the waste of a capsule which would otherwise be released immediately upon insertion of the magazine.

Formed within the fourth type of rotary magazine (623) is a pair of capsule release cam tracks (617), one track being situated towards each end of the magazine. At the open end which is the drive end of the magazine these tracks are defined by a wall (637) of the outer casing and track pieces (638) (FIG. 33) integrally mounted in the outer casing, and at the closed or non-drive end they are defined by track pieces (638). The cam tracks (617), the track pieces (638), and the end cap (633) are stationary parts and may be formed integrally with or separate from the outer casing (636), depending upon the method of assembly of the magazine. The locus of the tracks is the same as that shown in FIG. 9.

The piercing pins (601) are formed with pegs (619) as followers to fit into the release tacks (617) between the track pieces. As the rotor comprising end hubs (632) and central hub (631) rotates and the pins (601) rotate with them, so the pegs (619) of the pins (601) follow the tracks (617). The pins are formed to be axially movable within the rotor comprising end hubs (632) and central hub (631).

As the drive pegs (619) of the pins follow the tracks (617) they are caused, at the bulges, to move out towards the ends of the magazine. The bulges are situated at the 'use position', i.e. where a recess in a magazine inserted into the inhaler is part of the swirling chamber (529) of the inhaler and a capsule in that recess is to be used. At this point, therefore, the two piercing pins (601) holding that capsule move apart, thereby unplugging their capsule (25) and releasing it. Thus, the capsules are plugged tightly until their recesses reach this 'use position' where they are released. When, after use, they are returned to their recesses by the ejector plate (517) of the inhaler the capsules are kept in their recesses as the magazine is rotated. As a recess is rotated away from the 'use position', the drive pegs of the pins (601) of that recess continue to follow the cam tracks (617); they come towards each other again, and re-plug the used capsule. This is useful, not only in preventing capsules from moving about freely, possibly jamming the magazine, but also in preventing any residual powder in the spent capsules from escaping to contaminate the inhaler, and causing it to need further cleaning.

In the above described fourth magazine embodiment although the capsules may be pierced before loading into the magazine, the pins are so shaped that they can, if desired, pierce the capsules upon loading of the magazine with the capsules. Alternatively they can be shaped so that they merely provide a plug for pre-pierced capsules.

Although in both described magazines the mechanism which causes a capsule to be released, that is the cam tracks and protrusions, is part of the magazine itself, this does not have to be the case. To simplify the magazines, there may be tracks or protrusions associated with, or in, the walls of the magazine chamber (39, 339, 539) which cause the capsules to be released at the proper 'use position'. Similarly the magazines could be provided with piercing pins which are guided by tracks in the magazine chamber walls to pierce a capsule just before use. Such tracks or protrusions in the walls of the magazine chamber could lead to simplified rotary magazines and prevent the need for a new magazine to be inserted in a particular position rather than just in a particular orientation.

The present invention may be used with many types of inhalation mechanism whereby the contents of a capsule are extracted or drawn out. However, it is preferable that it should be used in a system where the contents of a capsule are drawn out via holes formed or pierced in the capsule, preferably in its ends. More particularly the contents are extracted from a capsule by a combination of pneumatic action, centrifugal action, and impact of a pierced capsule with the lateral wall of the swirling chamber.

The inhalation system is described with reference to all of the above-described inhaler embodiments. There is provided a swirling chamber (29, 329, 529) having a substantially circular peripheral side wall (30, 330, 530) adjoining flat end walls defined by a mesh (37, 337, 537) and a wall. There is a chordal recess (41, 341, 541) in the side wall which is part of the rotary magazine (23, 323, 623, 723) which forms one part of the chamber (29, 329). It is from this recess that a capsule is presented, tangentially to the circular peripheral walls, and to which the capsule will return after use.

Figure 17:
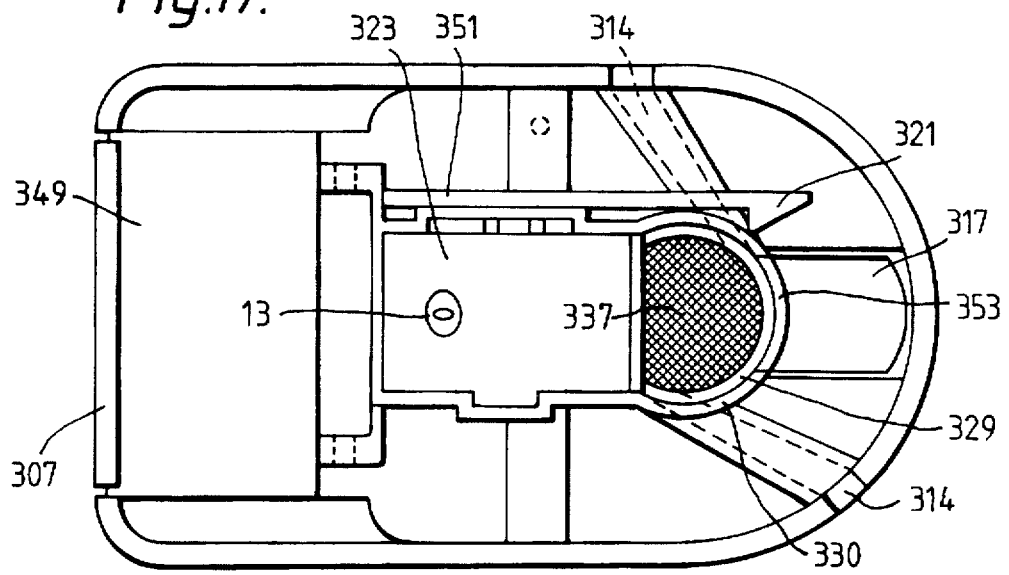
FIG. 17 is an underneath plan view of the inhaler of FIG. 15 with the outer cover removed.

The chamber (29, 329, 529) furthermore communicates with the two air inlets (14, 314, 514) which clearly generate a swirling motion in the chamber about an axis which is generally central of this chamber and extends perpendicular to the plane of the paper in FIGS. 4, 17 and 28, as air is aspirated through the mouthpiece nozzle (3, 303, 503). There is a direct passage between the chamber (29, 329, 529) and the mouthpiece (3, 303, 503) in which the only barrier is the mesh (37, 337, 537). Since, in the present invention the capsule will remain in one piece and, at least in the first inhaler embodiment, there should be no other fragments, it is not necessary that the mesh should be particularly fine (which could possible result in it trapping particles of the contents of the capsule) but instead it may be quite coarse, needing only to prevent the capsule itself from leaving the swirling chamber (29, 329, 529) whilst allowing the capsule to rotate around the chamber without being trapped. This reduces the air flow throttling effect of the mesh on the inhalation stream.

Once a fresh capsule is presented within the swirling chamber (29, 329, 529) through the use of the recharging mechanism, the operator simply inhales through the mouthpiece to generate the necessary swirling air stream into the swirling chamber (29, 329, 529) through the inlets (14, 314, 514). This same swirling action will, if necessary, detach the capsule from the recess (41, 341, 541) in the use position and will cause the capsule to rotate rapidly about the above-mentioned axis of rotation of the vertical swirling air flow in the chamber. The capsule is to be of a length shorter than the diameter of the chamber and this means that it is able to be spun round its transverse axis in the vertical air flow. At the same time the length of the capsule may allow it to contact the peripheral wall of the chamber so as to sustain impacts which help remove the contents, that is the pulverulent medicament, from within the capsule by percussive action.

This degree of impact with the walls of the chamber is enhanced by the presence of the recess (41, 341, 541) giving the chamber a generally non-symmetrical or eccentric appearance, resulting in random and rapidly occurring impacts which augment any centrifugal emptying of the spinning capsule shell. Further impacts may be sustained if the end tab of the ejector plate protrudes slightly in to the chamber or is recessed slightly, either case forming further impact surfaces. When inhalation is complete, the medicament will almost completely have been emptied from the capsule and indeed also from the chamber by being exhausted through the mesh.

Provided the inhaler is kept dry, and if the materials chosen for all appropriate parts, e.g. medicament-contacting parts, of the inhaler in accordance with the present invention are ones which have a relatively low electrostatic attraction for the contents of the capsule, the inhaler will not need regular cleaning when used by the same operator. The mesh may be of a material which is electrically conductive or is otherwise antistatic. Preferably it may be of a conductive polymer though it may be of a metal such as stainless steel.

With regard to all embodiments discussed above, the exact positioning of the magazine chambers, magazines, swirling chamber, mouthpiece etc. relative to each other is not important and may be varied in the inhaler. Any of the embodiments described could be altered whereby, having the same external shape, they could either provide piercing of the capsules within the device or use pre-pierced capsules.

The actual shape of the swirling chamber may also be varied in accordance with the present invention provided the capsule-emptying action is still achieved.

The magazines, which are loaded in the factory, may be assembled by clipping together or preferably by welding. If a magazine is welded it helps prevent possible tampering which, since this inhaler is for the provision of medicaments, could have very dangerous consequences.

It is possible that the inhalers of the present invention can be as automated and made as 'user friendly' as possible. As described herein, the mechanisms can be motorized and it is envisaged that logic circuits can be introduced whereby a magazine is prevented from going round more than once. Other features which such a logic system could include would be to provide a visual and/or audible alarm to indicate when the seventh or penultimate capsule or eighth or last capsule, of a magazine has been used, thereby helping to prevent someone from finding out that he has run out of capsules when he is most in need of them. Further features might include that the inhaler does not work once all the capsules have been used or possible that the magazine chamber cover will click open when the last capsule has been used, or even that the magazine can only be removed when it is in the orientation of just having been inserted, or of having had all its capsules used if this is different.

Not all these features need to be worked through a logic circuit. Whether or not such logic circuits are included, an indicator could be worked mechanically whereby the user can be readily made aware how many unused capsules remain, for example through the use of a window on the main body which shows an increasing amount of red as the capsules in the magazine are used up. Possibly there may be a keyway, or some other mechanical means whereby the magazine chamber cover may not be opened, or a magazine may not otherwise be removed when it is not in its start or finish position, that is the position it is in when it is inserted. (or the position it is in when all the capsules have been used, if this is different).

It is possible that in some of these embodiments the last capsule may be used and still left in the swirling chamber as the magazine is changed. The chamber may be provided with a removable cover for removing the last capsule, which cover could also be used for manual charging of the swirling chamber. Alternatively, or additionally, there may be provided mechanical or electrical means whereby a magazine cannot be changed until the last capsule has been ejected. Or, if the magazines have an empty recess in their blank positions, the last used capsule in a previous magazine can be placed in the empty recess of the new magazine.

If capsules are pre-pierced before loading into the magazine this produces less risk of small pieces of capsule likely to cause problems in the user's air tract as might happen in the case of an asthmatic. It is envisaged that capsules could be pre-pierced using a laser to make holds in each end before the capsules are loaded into a magazine and sealed thereon. With such capsules, and others where there is no danger from fragments of capsule, it might be possible to substitute the mesh in the swirling chamber by some form of a mixer to mix the capsule contents with the air, provided such a mixer preserves the chamber geometry and retains the capsule.

It is possible for devices according to the present invention to be provided with spare magazine or capsule chambers so that an inhaler user may always have a good supply of capsules with him. Another addition might be a mouthpiece cover pivoted or otherwise attached to the inhaler, provided to improve hygiene.

The method by which the capsules are loaded into the magazines is not particularly important, though it is preferable that in the case of some of these described magazines they are provided in an orientation whereby the blank position may be positioned in the 'use position' initially. It is envisaged that magazines could be re-used.

We claim:

1. A rotary magazine for use in an inhaler, comprising a plurality of recesses for holding pierced capsules, means for holding the capsules, means for plugging pierced holes in the capsules, and means to release said capsules one at a time from said magazine, wherein said holding means and plugging means are provided in a plurality of individual recesses.

2. A rotary magazine according to claim 1, wherein said holding means and said plugging means are integral.

3. A rotary magazine according to claim 1, wherein the holding means and plugging means are provided at both ends of the recesses.

4. A rotary magazine according to claim 3, wherein said plugging means comprise piercing means for piercing said capsules.

5. A rotary magazine according to claim 1, further comprising capsules loaded in said recesses.

6. A rotary magazine according to claim 5 wherein the capsules are provided with holes before they are loaded.

7. A rotary magazine according to claim 1, wherein the plurality of recesses are adapted to be rotated, one by one, to a use position within said magazine.

8. A rotary magazine according to claim 7 further comprising release tracks, wherein said capsule holding means further comprise track followers which follow said tracks as the recesses are rotated and wherein at said use position of said magazine the tracks are contoured whereby the followers move apart for releasing capsules held by said holding means at said use position.

9. A rotary magazine according to claim 7 further comprising catching means provided in the capsule at said use position, and raised portions formed on said holding means, wherein when a recess is rotated to the use position the raised portions on said holding means are rotated to the use position and are caught on the catching means, whereby they are moved apart for releasing a capsule held by the holding means at said use position.

10. A rotary magazine according to claim 1, wherein the plugging means further comprise sealing means for sealing pierced holes against the environment.

11. A rotary magazine according to claim 1, further comprising means which indicate the number of used or unused capsules.

12. An inhaler in combination with the magazine according to claim 1.

13. An inhaler comprising a capsule-emptying chamber, a nozzle through which air can be exhausted from said capsule-emptying chamber by inhalation, a magazine for providing one capsule at a time from a plurality of capsules to said capsule-emptying chamber through a use position in said magazine and ejecting means for removing a spent capsule from the capsule-emptying chamber into storage means within the inhaler.

14. An inhaler according to claim 13 wherein said ejecting means returns spent capsules to said magazine, and further comprising means to present further capsules to said capsule-emptying chamber through a use position in said magazine.

15. An inhaler according to claim 14, wherein the magazine is a rotary magazine.

16. An inhaler according to claim 15, wherein the magazine is removable and replaceable.

17. An inhaler according to claim 15, wherein the ejecting means removes a spent capsule from the capsule-emptying chamber and is moved to a position adjacent to the magazine before the magazine is rotated to present another capsule to the use position.

18. An inhaler according to claim 17, wherein said ejecting means is operative to remove spent capsules from the capsule-emptying chamber into recesses in the magazine from which capsules have previously been transferred to the capsule-emptying chamber.

19. An inhaler according to claim 18, wherein said ejecting means is operative to remove a spent capsule from the capsule-emptying chamber into the recess from which it was presented to said capsule-emptying chamber.

20. An inhaler according to claim 15, further comprising a drive mechanism for operating the ejecting means and the means to provide a further capsule.

21. An inhaler according to claim 15, wherein said magazine further comprises piercing means whereby said capsules are pierced when said magazine is loaded.

22. An inhaler according to claim 14 including a motor for operating said ejecting means and the means for presenting a further capsule.

23. An inhaler according to claim 14, further comprising means for preventing a magazine from providing the same capsule to the emptying chamber more than once.

24. An inhaler according to claim 23, wherein the means for preventing a magazine from providing the same capsule more than once comprises a logic circuit.

25. An inhaler according to claim 23, wherein the means for preventing a magazine from providing the same capsule more than once comprises a rotation stop for cooperating with an involute cam track of a rotor of the magazine extending over 360° of arc for preventing more than one turn of rotation of the rotor relative to a stator of the magazine.

26. An inhaler according to claim 13, wherein the ejecting means comprises an ejector plate having an end plate.

27. An inhaler according to claim 26, wherein said end plate is substantially arcuate in shape.

28. An inhaler according to claim 26, wherein the end plate forms an impact surface in the emptying chamber.

29. An inhaler comprising a swirling chamber having first and second generally parallel opposed walls and a peripheral wall with a chordal chamber recess therein, a nozzle through which air flow through said chamber can be induced by inhalation, and a magazine having recesses for capsules to be presented transversely to their lengths to said chamber, wherein said first and second walls are spaced apart by less than the length of the magazine recesses, the width of said swirling chamber is greater than the length of the magazine recesses, and said magazine recesses are sequentially presented to said chamber to from the chordal chamber recess.

30. An inhaler according to claim 29, wherein said magazine comprises a plurality of magazine recesses for housing capsules, and wherein the chamber recess is provided by the magazine recess at a use position in said magazine for presenting a capsule to said chamber.

31. An inhaler according to claim 30, further comprising means to rotate said magazine recesses to become said chamber recess at said use position one by one.

32. An inhaler according to claim 29, further comprising piercing means to pierce capsules within the inhaler.

33. An inhaler according to claim 32, wherein capsules in said magazine are pierced before the magazine is loaded into said inhaler.

34. An inhaler comprising a capsule-emptying chamber, a nozzle through which air can be exhausted from said capsule-emptying chamber by inhalation, a magazine for providing one capsule at a time from a plurality of capsules to the capsule-emptying chamber through a use position in said magazine, a motor for controlling operation of the magazine and provision of capsules to the capsule-emptying chamber, and ejecting means for removing a spent capsule from the capsule-emptying chamber into storage means within the inhaler.

35. An inhaler according to claim 34, wherein said magazine is a rotary magazine.

36. An inhaler according to claim 35, wherein said magazine comprises a plurality of recesses for holding capsules, and a capsule is presented to said capsule emptying chamber from a recess when said recess is in the use position.

37. An inhaler according to claim 36, further comprising an alarm means to indicate when the magazine has rotated every recess to the use position.

38. An inhaler according to claim 36, further comprising alarm means to indicate when the magazine has rotated all but one of said recesses to the use position.

39. An inhaler according to claim 38, wherein said alarm means provides an audible alarm.

40. An inhaler according to claim 38, wherein said alarm means provides a visual alarm.

* * * * *